US007790446B2

(12) United States Patent
Silla et al.

(10) Patent No.: US 7,790,446 B2
(45) Date of Patent: Sep. 7, 2010

(54) VECTORS, CELL LINES AND THEIR USE IN OBTAINING EXTENDED EPISOMAL MAINTENANCE REPLICATION OF HYBRID PLASMIDS AND EXPRESSION OF GENE PRODUCTS

(75) Inventors: Toomas Silla, Tartu (EE); Ingrid Tagen, Tartu (EE); Jelizaveta Geimanen, Tartu (EE); Kadri Janikson, Tartu (EE); Aare Abroi, Tartu (EE); Ene Ustav, Tartu (EE); Mart Ustav, Tartu (EE); Tiiu Mandel, Tartu (EE)

(73) Assignee: Kosagen Cell Factory Oü, Tartu (EE)

( * ) Notice: Subject to any disclaimer, the term of this patent is extended or adjusted under 35 U.S.C. 154(b) by 0 days.

(21) Appl. No.: 11/351,809

(22) Filed: Feb. 10, 2006

(65) Prior Publication Data

US 2006/0183230 A1    Aug. 17, 2006

Related U.S. Application Data

(60) Provisional application No. 60/652,390, filed on Feb. 11, 2005.

(51) Int. Cl.
*C12N 15/00* (2006.01)
*C12N 15/113* (2006.01)
*C07H 21/04* (2006.01)
(52) U.S. Cl. .................. 435/320.1; 536/23.1; 536/24.1
(58) Field of Classification Search ............. 435/320.1; 536/23.1, 24.1
See application file for complete search history.

(56) References Cited

U.S. PATENT DOCUMENTS 5,972,334 A * 10/1999 Denney, Jr. ............... 424/131.1
6,255,071 B1 * 7/2001 Beach et al. ............... 435/69.1
6,479,279 B2 * 11/2002 Ustav ....................... 435/320.1
6,605,281 B1 * 8/2003 Broker et al. .............. 424/199.1

2003/0129169 A1 * 7/2003 Krohn et al. ............... 424/93.21

OTHER PUBLICATIONS

Accession J02288.1 GI:332752.*
Mearini et al, FEBS Letters 547:119-124, 2003.*
Lepik et al, Virology 74(10):4688-4697, 2000.*
Papovaviruses (http://virus.stanford.edu/papova/biology.html; Nov. 25, 2004).*
U.S. Appl. No. 10/938,864, filed Oct. 13th, R Kunaparaju.
Silla, T. Haal, I, Geimanen, J, JAnikson, K, Abroi A, Ustav E and Ustav e. Journal of Virology 79 (24): 15277-15288.
Dorigo, O. et al. 2004. Development of a Novel Helper-Dependent . . . Journal of Virology, 78(12) p. 6556-6566.
Ilves, I. et al. 1999. Long-term Episomal Maintenance of Bovine . . . Journal of Virology, 73(5) 4404-4412.
Abroi A. et al. 2004. Analysis of Chromatin Attachmetn and Partitioning . . . Journal of Virology. 78(4) 2100-2113.
Wade-Martins R. et al. 1999. Long-term stability of large insert . . . Nucleic Acids Research 27(7) 1674-1682.
Bhattacharyya, S. et al. 1995. Murine Polyomavirus and Simian . . . Journal of Virology 69(120 7579-7585.
Li, R. Knight J, Bream G, Stenlund A and Botchan M. 1989. Specific recognition nucleotides . . . Genes and Dev. 3: 510-526.

* cited by examiner

*Primary Examiner*—Kevin K. Hill
(74) *Attorney, Agent, or Firm*—Dodds and Associates; Leea Susanne Somersalo; John M. Dodds

(57) ABSTRACT

This disclosure shows that the BPV-1 E2 protein-dependent minichromosome maintenance element (MME) comprised of E2 multimeric binding sites can provide the stable maintenance replication function to the mouse polyomavirus (PyV) core origin plasmids in the presence of BPV-1 E2 protein and PyV large T-antigen (LT). MME dependent plasmids are lost with the frequency of 6% per generation. Significantly long stable maintenance replication can also be provided without selection pressure. We also demonstrate that PyV core origin maintenance function/replication activation could be provided by Epstein-Barr virus Family of repeats and EBNA1 protein. The maintenance of the Polyomavirus core origin plasmid was characterized by 13% loss of the plasmid during one cell generation in the case of EBV FR harboring plasmids. Our data clearly indicate that maintenance functions from different viruses can provide segregation/partitioning function to different heterologous origins in variety of cells and can be used in expression of gene products.

16 Claims, 10 Drawing Sheets

| Construct | | Rate of loss per cell generation (%) |
|---|---|---|
| pMMEG | 1 series | 5.5 |
| pMMEG | 2 series | 6.5 |
| pMMEG* | 1 series | 6.6 |
| pMMEG* | 2 series | 5.9 |
| pFRG* | 1 series | 13.1 |
| pFRG* | 2 series | 13.6 |
| Control plasmids | | |
| pEGFP-C1 | | 21.7 |
| pdEGFP-N1 | | 29.8 |

A

B

```
                        SEQUENCE LISTING

<160> NUMBER OF SEQ ID NOS: 14

<210> SEQ ID NO 1
<211> LENGTH: 12
<212> TYPE: DNA
<213> ORGANISM: Bovine Papillomavirus
<220> FEATURE:
<221> NAME/KEY: misc_feature
<222> LOCATION: (1)..(12)
<223> OTHER INFORMATION: alternative E2 binding site
<220> FEATURE:
<221> NAME/KEY: misc_feature
<222> LOCATION: (5)..(8)
<223> OTHER INFORMATION: any nucleotide

<400> SEQUENCE: 1
accgnnnncg gt                                                           12

<210> SEQ ID NO 2
<211> LENGTH: 154
<212> TYPE: DNA
<213> ORGANISM: Mouse polyomavirus
<220> FEATURE:
<221> NAME/KEY: misc_feature
<222> LOCATION: (1)..(154)
<223> OTHER INFORMATION: PyV core origin

<400> SEQUENCE: 2
cctagaatgt ttccacccaa tcattactat gacaacagct gtttttttta gtattaagca       60
gaggccgggg gcccctggcc tccgcttact ctggagaaaa agaagagagg cattgtagag      120
gcttccagag gcaacttgtc aaaacaggac tggc                                  154

<210> SEQ ID NO 3
<211> LENGTH: 19
<212> TYPE: DNA
<213> ORGANISM: Mouse polyomavirus
<220> FEATURE:
<221> NAME/KEY: misc_feature
<222> LOCATION: (1)..(19)
<223> OTHER INFORMATION: Py4963

<400> SEQUENCE: 3
agggagctac ttcctgatg                                                    19

<210> SEQ ID NO 4
<211> LENGTH: 15
<212> TYPE: DNA
<213> ORGANISM: Mouse polyomavirus
<220> FEATURE:
<221> NAME/KEY: misc_feature
<222> LOCATION: (1)..(15)
```

```
<223> OTHER INFORMATION: PyV174  primer

<400> SEQUENCE: 4
ctaccactcc gactt                                                          15

<210> SEQ ID NO 5
<211> LENGTH: 12
<212> TYPE: DNA
<213> ORGANISM: Bovine Papillomavirus
<220> FEATURE:
<221> NAME/KEY: misc_feature
<222> LOCATION: (1)..(12)
<223> OTHER INFORMATION: alternative E2 binding site

<400> SEQUENCE: 5
accgttgccg gt                                                             12

<210> SEQ ID NO 6
<211> LENGTH: 7
<212> TYPE: DNA
<213> ORGANISM: Bovine Papillomavirus
<220> FEATURE:
<221> NAME/KEY: misc_feature
<222> LOCATION: (1)..(7)
<223> OTHER INFORMATION: spacer

<400> SEQUENCE: 6 gatctgt                                                                    7

<210> SEQ ID NO 7
<211> LENGTH: 2
<212> TYPE: DNA
<213> ORGANISM: Bovine papillomavirus
<220> FEATURE:
<221> NAME/KEY: misc_feature
<222> LOCATION: (1)..(2)
<223> OTHER INFORMATION: spacer

<400> SEQUENCE: 7 cg                                                                         2

<210> SEQ ID NO 8
<211> LENGTH: 21
<212> TYPE: DNA
<213> ORGANISM: Bovine papillomavirus
<220> FEATURE:
<221> NAME/KEY: misc_feature
<222> LOCATION: (1)..(7)
<223> OTHER INFORMATION: spacer
<220> FEATURE:
<221> NAME/KEY: misc_feature
<222> LOCATION: (8)..(19)
<223> OTHER INFORMATION: alternative BPV E2 binding site
<220> FEATURE:
<221> NAME/KEY: misc_feature
<222> LOCATION: (11)..(16)
<223> OTHER INFORMATION: any nucleotide
<220> FEATURE:
<221> NAME/KEY: misc_feature
<222> LOCATION: (19)..(21)
<223> OTHER INFORMATION: spacer

<400> SEQUENCE: 8
gatctgtacc nnnnnnggtc g                                                   21

<210> SEQ ID NO 9
<211> LENGTH: 11
<212> TYPE: DNA
<213> ORGANISM: Human Papilloma virus
```

```
<220> FEATURE:
<221> NAME/KEY: misc_feature
<222> LOCATION: (1)..(11)
<223> OTHER INFORMATION: alternative HPV E2 binding site

<400> SEQUENCE: 9
accgaaacgg t                                                              11

<210> SEQ ID NO 10
<211> LENGTH: 18
<212> TYPE: DNA
<213> ORGANISM: Epstein Barr Virus
<220> FEATURE:
<221> NAME/KEY: misc_feature
<222> LOCATION: (1)..(18)
<223> OTHER INFORMATION: Alternative EBNA1 binding site

<400> SEQUENCE: 10
gggtatcata tgctgact                                                       18

<210> SEQ ID NO 11
<211> LENGTH: 18
<212> TYPE: DNA
<213> ORGANISM: Epstain Barr Virus
<220> FEATURE:
<221> NAME/KEY: misc_feature
<222> LOCATION: (1)..(18)
<223> OTHER INFORMATION: alternative EBNA 1 binding site

<400> SEQUENCE: 11
gggtatcata tgctgact                                                       18

<210> SEQ ID NO 12
<211> LENGTH: 18
<212> TYPE: DNA
<213> ORGANISM: Epstein Barr virus
<220> FEATURE:
<221> NAME/KEY: misc_feature
<222> LOCATION: (1)..(18)
<223> OTHER INFORMATION: alternative EBNA 1 binding site

<400> SEQUENCE: 12
ggatagcata tgctaccc                                                       18

<210> SEQ ID NO 13
<211> LENGTH: 18
<212> TYPE: DNA
<213> ORGANISM: Epstein Barr virus
<220> FEATURE:
<221> NAME/KEY: misc_feature
<222> LOCATION: (1)..(18)
<223> OTHER INFORMATION: alternative EBNA1 binding site

<400> SEQUENCE: 13
ggatagcata tactaccc                                                       18

<210> SEQ ID NO 14
<211> LENGTH: 630
<212> TYPE: DNA
<213> ORGANISM: Epstein barr virus
<220> FEATURE:
<221> NAME/KEY: misc_feature
<222> LOCATION: (1)..(630)
<223> OTHER INFORMATION: alternative FR-element

<400> SEQUENCE: 14
ctagtcgggt atcatatgct gactgtatat gcatgaggat agcatatgct acccggatac         60
```

-continued

```
agattaggat agcatatact acccagatat agattaggat agcatatgct acccagatat    120
agattaggat agcctatgct acccagatat aaattaggat agcatatact acccagatat    180
agattaggat agcatatgct acccagatat agattaggat agcctatgct acccagatat    240
agattaggat agcatatgct acccagatat agattaggat agcatatgct atccagatat    300
ttgggtagta tatgctaccc agatataaat taggatagca tatactaccc taatctctat    360
taggatagca tatgctaccc ggatacagat taggatagca tatactaccc agatatagat    420
taggatagca tatgctaccc agatatagat taggatagcc tatgctaccc agatataaat    480
taggatagca tatactaccc agatatagat taggatagca tatgctaccc agatatagat    540
taggatagcc tatgctaccc agatatagat taggatagca tatgctatcc agatatttgg    600
gtagtatatg ctacccatgg caacattaga                                     630
```

VECTORS, CELL LINES AND THEIR USE IN OBTAINING EXTENDED EPISOMAL MAINTENANCE REPLICATION OF HYBRID PLASMIDS AND EXPRESSION OF GENE PRODUCTS

PRIORITY

This application claims priority of provisional patent application No. 60/652,390 filed Feb. 11, 2005, which is incorporated herein by reference.

SEQUENCE LISTING

This application contains sequence data provided on a computer readable diskette and as a paper version. The paper version of the sequence data is identical to the data provided on the diskette.

TECHNICAL FIELD OF THE INVENTION

The present invention relates to extended maintenance replication of hybrid plasmids. The present invention also relates to extended episomal replication of hybrid plasmid in eucaryotic cell lines. The present invention also relates to expression of gene products in eucaryotic cell lines.

BACKGROUND OF THE INVENTION

Several eukaryotic DNA viruses maintain their genomes as extrachromosomal multicopy nuclear episomes in proliferating host cells. Such episomal maintenance is characteristic of latent infection of the Bovine papillomavirus type 1 (BPV-1), Epstein-Barr Virus (EBV) as well as for Kaposi sarcoma associated Human herpesvirus type 8 (HHV8). The latency of the viral genome in dividing cell population requires activity of the viral genome at the two phases of the cell cycle: the viral genome replication during the S phase and proper segregation and partitioning of the replicated genomes into daughter cells during the host cell mitosis. For BPV-1 and two members of the gammaherpesvirus family—EBV and HHV8 an effective segregation of viral genomes into daughter cells and nuclear retention during mitosis is mediated through a single viral protein serving as a molecular linker, which attaches viral genomes to the host mitotic chromosomes. This linker protein is a viral regulatory protein E2 for BPV-1, viral transactivator EBNA1 for EBV and viral transcription repressor LANA1 for HHV8.

For initiation of the BPV-1 DNA replication in vivo, minimal origin region in cis and two viral proteins—E1 and E2, in trans, are absolutely essential. However, the minimal origin (MO) is not sufficient for stable extrachromosomal replication in dividing cells. An additional element, the Minichromosome Maintenance Element (MME) ensures the long-term episomal persistence of the genome in the presence of viral E1 and the E2 proteins in the dividing cells. In the BPV-1 genome in total 17 E2 protein binding sites with different affinity to E2 can be identified: 12 of these are locating in the noncoding upstream regulatory region (URR). We have shown that the minichromosome maintenance element (MME) activity can be provided by the subset of the E2 binding sites. The function of multimeric E2 protein binding sites in the stable maintenance of the BPV-1 genomes is to provide the anchoring function for the E2 protein, which therefore tethers MME containing plasmids to mitotic chromosomes. This linkage between the BPV-1 genome and host chromatin ensures also that the viral genome is targeted to the nucleus when the nuclear membrane is reassembled during mitosis. In the case of EBV, the stable maintenance of replicated genomes is achieved due to the EBNA1 protein and FR-element, which is comprised of multimeric EBNA1 protein binding sites.

We have shown that the BPV1 E2 protein dependent MME (Abroi et al. 2004) and EBV EBNA1 dependent FR (Mannik, Janikson and Ustav, unpublished) segregation/partitioning activities function independently from replication of the plasmids. The stable-maintenance funcion of EBNA1/FR has been used to ensure long-time episomal maintenance for cellular replication origins. The E2/MME-dependent stable-maintenance function has never been tested with heterologous replication origins.

Transfection or infection of permissive cells with polyomavirus genome or replicator results in amplificational replication leading to cell death due to the over-replication. The mechanism of the BPV-1 origin based episomal replication is more complex and controlled. On one hand the first amplificational replication step, resembling in many aspects polyomavirus lytic over-replication is crucial for establishment of the stable episomal replication of the papillomavirus DNA. Such replication leads to increase of expression level of the viral proteins and copy-number of the viral genome. Increase of the E1 protein concentration, however, over certain limit induces the "onion-skin" type replication of the BPV-1 origin and generation of the replication intermediates having tendency for high frequency of DNA rearrangements and integration of the fragments of the viral DNA into chromosomal DNA. To maintain the stability and intactness of the viral genome, virus has to apply certain mechanism to assure proper balance between initiation and elongation of replication fork as well as segregation/partitioning of the viral plasmids during cell division The stable episomal maintenance systems described earlier (U.S. Pat. No. 6,479,279) were provided with homologous replication origins. Characteristic for these systems is for example a high mutation frequency, especially recombination. Furthermore, the system does not give stable replication in single cells but part of the cells lose their plasmid in every generations. This fact creates serious limits for the system to be used for example in protein production. Nilsson et al (1991) describe a system providing an enhancer function, but that system has serious limitation in terms of stability. The present disclosure provides improvements over the problems encountering prior systems. The present disclosure provides an extended episomal maintenance system with heterologous replication origin. The heterologous system according to this disclosure can be used in combination with homologous systems. The present disclosure provides a system where plasmids containing core polyoma virus origin (not containing enhancer function) partition into daughter cells. The system according to this disclosure provides a system where a unique configuration of polyoma virus origin (core polyomavirus origin not containing enhancer function) is stable and is segregated in the presence of helper proteins. An advantage of the present system is that episomal state of chimeric origins is maintained without rearrangement. The present invention further provides a possibility to combine vectors with polyoma virus origin and papilloma origin into a single cell, thereby enabling expression of more than one different recombinant proteins or RNAs in one cell. A further advantage of the current system is that it provides stable episomal maintenance in the cell that lasts up to several months as opposed to all previous systems which provide maintenance of maximally a few weeks; e.g. U.S. patent application Ser.

No. 10/938,864 describes a system capable of stable episomal replication lasting about two weeks.

The problem that we aimed to solve is that stable expression of gene products in cell systems is costly and time consuming. This problem has been solved in the present disclosure by transient expression of gene products in cells. Since the genes of interest are replicated and maintained outside the chromatin in the nucleus, the vectors go to the progeny in cell division and segregation and with the method of the current disclosure the expression of the gene products can be continued for months.

Development of stable expression in cell lines takes usually several months or even years. The transient system that we describe here is much faster and therefore useful and novel. On the other hand the transient systems so far known have a very limited half-life; i.e. maximally a couple of days. In addition, those systems may need construction of recombinant viruses which makes the systems expensive and very time consuming. Our system provides a marked improvement to the existing art; the system according to this disclosure provides a transient expression system that maintains the expression levels for several weeks and even up to several months.

The present disclosure provides a possibility to develop stable cell lines when the vector according to this disclosure contains a selection marker and the cells are cultivated on a medium containing the selective agent. The present disclosure also provides a possibility to express gene products in a cell line for shorter time when the vector does not contain a selection marker. However, even without using selection pressure the current system provides stable maintenance that lasts longer than with any other comparable system previously known.

The present disclosure further enables development of a multi-replicon expression system, where more than one gene products are expressed from different replicons and the replicons are locating in same cell. Such a mechanism is useful for example to express different subunits of antibodies or enzyme subunits in one cell or to study interactions of macromolecules expressed in the cell.

An object of the present disclosure is to provide a mechanism to extended episomal maintenance of polyoma virus core origin.

Another object of the present disclosure is to provide a mechanism to extended episomal maintenance of polyoma virus core origin without selective pressure.

Another object of the present disclosure is to provide constructs in conjunction with the segregations/partitioning elements from BPV1 or EBV.

A still further object of the present disclosure is to provide cell lines capable of supporting the replication and episomal maintenance of hybrid plasmids.

A still further object of the present disclosure is to provide a transient system for long lasting expression of gene products in eukaryotic cells.

An even further object of the present disclosure is to provide cell lines harboring more than one different vectors and thereby providing expression of more than one different genes of interest.

An even further object of the present disclosure is to provide a transient system for long lasting production therapeutic, prophylactic or endotoxine free gene products for diagnostic and other applications in eukaryotic cells.

Another object of the present disclosure is to provide a transient system for long lasting production of RNA or proteins in eukaryotic cells. The cells can be cultivated and gene products can be expressed in small and large scale; from laboratory flasks and Petri dishes up to big fermenters.

In order to study coordination between initiation and elongation of replication and segregation/partitioning of the episomal origin plasmids, we designed several hybrid replication origins comprising polyomavirus replication origin and minichromosome maintenance element (MME) of the BPV1. We analyzed the effect of the PyV enhancer and E2 dependent enhancer on the functionality of the PyV core origin in establishing of the extended episomal maintenance replication of the hybrid origins in the cell lines expressing E2 proteins and PyV large T antigen (LT). Additionally, we studied the functions of the BPV1 E2 protein necessary for maintenance function of the hybrid origins and found that transcriptional activation function of the E2 protein is unable to promote the establishment of the stable replication. Similar hybrid origins comprising the EBV FR-element and polyomavirus replication origin were constructed and studied in the cell lines expressing EBNA1 and polyomavirus large T antigen (LT). Our data suggest convincingly that segregation/partitioning functions of the BPV-1 and EBV can effectively be used for extended episomal maintenance of the polyomavirus core origin.

Bovine papillomavirus type 1, Epstein-Barr virus and Human Herpesvirus type 8 genomes are stably maintained as episomes in dividing host cells during latent infection. Segregation/partitioning function is given to these origins by single viral specific DNA-binding protein and multimeric protein binding sites. This disclosure shows that the BPV-1 E2 protein-dependent MME comprising E2 multimeric binding sites can provide the extended maintenance replication function to the mouse polyomavirus (PyV) core origin plasmids in the presence of BPV-1 E2 protein and PyV large T-antigen (LT), but fail to do so for the complete PyV origin. In mouse fibroblast cell-lines expressing PyV LT and BPV-1 E2 (COP5/E2), the plasmids carrying PyV core origin linked to at least five multimeric E2 protein binding sites show the capacity for long term episomal replication, which can be monitored for more than 5 months (under selective conditions). Overall structural integrity as well as the intactness of domains of BPV-1 E2 are required for efficient episomal maintenance. Our data show clearly that the large T antigen dependent replication function of the polyomavirus and extended maintenance functions of the BPV-1 are compatible in certain configurations. Further quantitative analysis of the loss of the episomal plasmids carrying hybrid origin showed that MME dependent plasmids are lost with the frequency of 6% per generation. We also constructed the plasmids where PyV core origin maintenance function/replication activation could be provided by Epstein-Barr virus Family of repeats (FR-element) and EBNA1 protein. The maintenance of the Polyomavirus core origin plasmid was characterized by 13% loss of the plasmid during one cell generation in the case of these plasmids. Our data clearly indicate that maintenance functions from different viruses are interchangeable and can provide segregation/partitioning function to different heterologous origins in variety of cells and be used in expression of gene products.

BRIEF DESCRIPTION OF THE FIGURES

FIG. 8. Rates of plasmid loss calculated from the data in FIG. 7. Rates observed for two control plasmids lacking replication origin are shown as well.

DETAILED DESCRIPTION OF THE INVENTION

Figure 1:
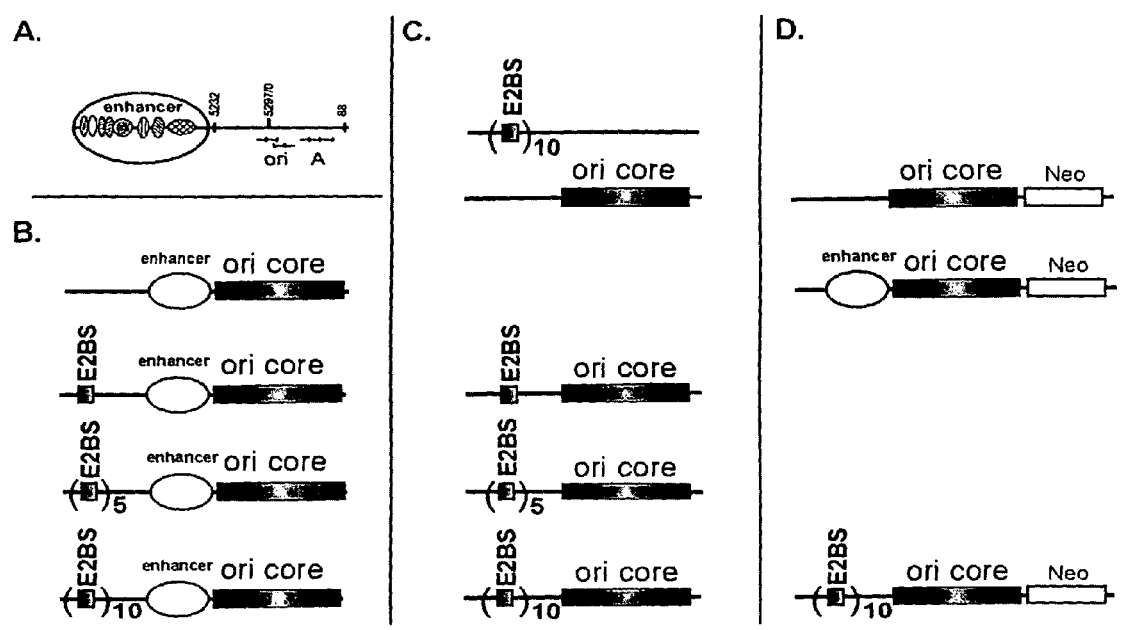
FIG. 1. Schematic representation of PyV hybrid origin constructs. (A) Schematic representation of PyV wild type origin, comprising the enhancer sequence and the core origin. All the plasmids were constructed using pUC19 as backbone as described in Materials and Methods. (B) Plasmids, which share PyV wild-type origin (enhancer element represented as an open oval ring, core origin represented as filled rectangular) and in addition one, five or ten E2 binding sites (E2BS) (indicated as shadowed square; number of E2 binding sites is indicated with corresponding number). (C) Constructs, where the wild-type enhancer element is removed or replaced by E2 binding sites. (D) Reporter-constructs, which carry a eukaryotic selection cassette, such as the neomycin resistance gene (indicated as an open rectangular), which makes it possible to screen transfected cells in extended maintenance assays.

Definitions:
In this disclosure the following terms are used as defined below:

"Papillomavirus" refers to a member of the papilloma family of viruses, including but not limited to bovine papillomavirus (BPV) and human papillomavirus (HPV).

"Polyomavirus" refers to a member of polyoma family of viruses, including but not limited to mouse polyomavirus (PyV).

"Polyomavirus core origin" refers to a minimal cis-sequence within a polyomavirus that is necessary for initiation of DNA synthesis. The PyV core origin is essentially according to SEQ ID NO: 2. The core origin of PyV is located at nucleotides 5232-5297/1-88 in total 154 bp (5232 and 88 included) in sequence PLY2CG (Genebank accession number J02288). The polyoma core origin is also referred as PyV core origin or as minimal core origin.

The Minimum origin (MO) of BPV1 is defined as described in U.S. Pat. No. 6,479,279.

FR element refers to Epstein-Barr virus family of repeats. It comprises at least 16 EBNA1-binding sites. SEQ ID NO: 14 gives nucleotide sequence of one alternative synthetic FR-element. In this element 20 EBNA binding sites were used. The EBNA 1-binding sites in the FR-element do not need to be similar to each other. The EBNA1-binding sites may be according to any one of SEQ ID NO: 10 to 13.

"EBNA1" refers to viral transactivator for EBV and is encoded by nt 7421-8043 in EBV sequence with Genbank accession number V01555.

"E1" refers to the protein encoded by nt 849-2663 of BPV subtype1, or to nt 932-2779 of HPV of subtype 11, or to equivalent E1 proteins of other papillomaviruses, or to functional fragments or mutants of a papillomavirus E1 protein, i.e. fragments or mutants of E1 which possess the replication properties of E1.

"E2" refers to the protein encoded by nt 2594-3837 of BPV subtype 1; or to nt 2723-3823 of HPV subtype 11, or to equivalent E2 proteins of other papillomaviruses, or to functional fragments or mutants of a papillomavirus E2 protein, i.e. fragments or mutants of E2 which possess the replicating properties of E2.

"Minichromosomal maintenance element" (MME) refers to a region of the papilloma viral genome to which viral or human proteins essential for papilloma viral replication bind, which region according to this invention is essential for stable episomal maintenance of core origin in a host cell. Preferably, the MME is a sequence containing multiple binding sites for E2. According to this disclosure the MME contains at least 5 E2 binding sites. The sequential binding sites which constitute the MME need not be identical in sequence, but must be able to bind E2.

"E2 binding site" (E2BS) refers to the minimum sequence of papillomavirus double-stranded DNA to which the E2 protein binds. E2 binding site may be of BPV or of HPV. The affinities of the E2 binding sites vary and according to this disclosure E2 binding site means a high affinity binding site. The E2 binding site may be according to SEQ ID NO: 1, preferably it is according to SEQ ID NO: 5. It may also be according to SEQ ID NO:9. In the vectors according to this disclosure the repetitive E2 binding sites are separated by spacers (SEG ID NO:6 and SEQ ID NO:7).

"Heterologous replication origin" refers to a system where the replication origin locates in a vector containing MME or FR-element of another virus species.

"A host cell" which is stably transformed according to the disclosure is a eukaryotic cell and preferably a mammalian cell, most preferably a human, mouse or hamster cell. The cell may be derived from any tissue. The host cell may be derived from CHO (hamster), COP (mouse) or human cell line 293.

"A gene of interest" refers to a gene encoding a gene product of interest such as a protein or RNA of interest.

'A gene product' refers to a product of the gene of interest. The product may be an expression product on RNA level or it can as well be an expressed protein or peptide. The gene products may be used for example as therapeutic or prophylactic purposes. The gene products may be endotoxine free products for diagnostic purpose. These uses are exemplary only and one skilled in the art would realize that there are other purposes as well according to this disclosure.

"Helper protein" refers to various viral proteins including viral regulatory proteins E1, E2, EBNA1, and LT.

We describe here a mechanism of extended replication of chimeric origins. We have developed PyV origin based constructs in conjunction with the segregation/partitioning elements from the BPV-1 or EBV and the cell lines capable of supporting the replication and episomal maintenance of these plasmids. Polyomaviruses exhibit replication patterns that are uncoupled from the regulatory mechanisms of the host cell, so that each viral genome replicates many times within each cell cycle to the maximal level. The complete polyomavirus origin (wild type origin) includes transcriptional and replicational enhancer sequences, which dictate the origin activity and the efficiency of replication in specific cells by determining the availability of the replication factors and nucleotides. Papillomavirus origin replication control is similar to polyomavirus replication in the first, amplificational phase of the replication. However, in the latent replication phase copy number control mechanism is applied, which assures the controlled initiation of replication of the episomal viral genome in the latent replication phase. Epstein-Barr virus (EBV) uses entirely cellular replication machinery for initiation of the latent origin oriP replication, which strictly replicates once per cell cycle. Although the BPV-1 and polyomaviruses use the host replication machinery for viral genome replication, the initiation of replication is achieved by viral factors, while for stable maintenance with the EBV entirely cellular initiation and elongation machinery is used. The polyomavirus replicational enhancer can be exchanged with binding sites for different factors such as c-Jun and Gal4, without loosing its ability to promote replication (Guo et al., 1996). The inventive step in this disclosure includes the finding that substitution of the wild-type PyV enhancer with at least five synthetic binding sites for the BPV-1 protein E2 (SEQ ID NO: 1), can replace replication enhancer function and makes it dependent on E2 protein. Surprisingly, addition of five or ten E2 binding sites to PyV wt origin did not cause additional replication activation. Therefore, the viral origin seem to achieve in a host cell a maximum activity when a strong enhancer is present and after that point enhancement of replication is not possible, even if additional enhancer elements are added. This may be because of limitation of cellular factors or saturation of the nucleus with the active genetic elements. Accordingly, we observed many dead cells after transfection with PyV wt origin constructs.

It is known that E2 protein of the BPV-1 and EBNA1 protein of the EBV are necessary and sufficient for linking of the MME containing plasmids to the chromatin. The novelty of this disclosure includes the finding that MME functions outside of its natural replication origin; all previous studies are done in the context of BPV-1 origin or with non-replicating plasmids. Using PyV origins linked to MME gives us the tool for studying MME universal functions and its compatibility with different replicators. Using PyV origin based chimeric constructs, we can study MME functioning in the replicating system in the absence of other BPV-1 proteins and genomic sequences. This disclosure shows that MME is functional in PyV origin based system. Interestingly, in the heterologous system MME provides extended maintenance function only for constructs, which contain PyV minimal core origin. In the case of wt PyV origin very strong transient replication was observed, however, it was impossible to rescue stable episomal replication of these plasmids, even after antibiotic selection for origin constructs. It is important to note that stably maintained constructs were in episomal state, no integration to host chromosomes was detected. Clearly, successful nuclear maintenance and partitioning of replicating MME reporters in proliferating cells is sensitive for replication level. Thus, for proper function of MME it is important to have balance between replication initiation/activation and stability element to secure the functioning of the episomal genetic element.

Structural intactness of E2 protein is very important in order to provide MME dependent partitioning. Recent study from our laboratory showed that single point mutation may affect E2 protein chromatin attachment or URR chromatin attachment, but moderately change replication or transcription activities. Such mutant proteins, E39A and R68A were used to analyze the possibility that PyV origin in conjunction with MME is stably maintained because of E2 protein moderate transcription activation properties. Our results show clearly that chromatin attachment activity of E2 protein is essential to provide stable maintenance for chimeric constructs used in this study and random partitioning of the episomal plasmids cannot provide reliable mechanism for extended episomal maintenance of the plasmids even in the presence of selection for the episomal selection marker. Therefore as shown in this disclosure MME mediated partitioning in conjunction with PyV core origin or its natural BPV-1 origin is achieved by using the same strategy which is described here.

Minichromosome Maintenance Element is Compatible with Different Replicators.

According to the present disclosure BPV-1 E2 protein-dependent Minichromosome Maintenance Element (MME) and EBV EBNA1 protein-dependent FR-element can provide extended maintenance functions to the PyV core origin plasmids in the presence of viral trans-factors. We have used stable replication assay and flow cytometric EGFP reporter expression assay for the analysis of the kinetics of the extended maintenance of the episomes. In the case of the BPV-1 and PyV the origin of replication is fired several times during their amplificational replication in host cell S-phase and even during the stable replication of the BPV-1 the origin is not restricted to precisely once in each cell cycle. At the same time the EBV latent origin oriP replicates strictly once per cell cycle, the same way as chromosomal DNA. The present disclosure suggests that the extended maintenance of the episomes provided by the function of MME or FR-element, is not connected to the mode of replication of the episome. FR-element can provide an extended maintenance function to both types of origins—in its natural context within EBV latent origin oriP and in our hybrid replicon together with PyV minimal origin (SEQ ID NO:2). The present disclosure also shows that the replication function is not connected to the stable maintenance function of the virus—replication origins of different viruses can be combined with different stable maintenance elements without the loss of either function. It has been shown previously that the cellular receptors of BPV-1 E2 protein and EBV EBNA1 protein, which link the episomes to mitotic host chromatin and therefore provide the stable maintenance function, are different. The present disclosure suggests that the different localization of the episome on mitotic chromosomes does not interfere with the replication of PyV minimal replication origin.

The Rate of Loss of Episomal Plasmids is Lower than in Control Plasmids

We have analyzed the episomal maintenance of the pMMEG, pMMEG* and pFRG* plasmids (Materials and Methods) in cells cultured without geneticine selection. These plasmids contained PyV minimal core origin (SEQ ID NO: 2) and either BPV-1 Minichromosome maintenance element (MME) or EBV FR-element. The viral trans-factors (either PyV LT and BPV 1 E2 or PyV LT and EBV EBNA 1 protein) were stably expressed in the cell line. For the analysis of the plasmid loss we measured the expression of the reporter gene EGFP (or d1EGFP) with flow cytometry. In the case of plasmids containing the PyV minimal core origin and BPV-1 MME the rate of episomal loss was 6% per cell division in the absence of geneticine selection. For plasmids containing PyV minimal origin and EBV FR-element, the rate of episomal loss was faster (~13%), but compared to the 22-30% rate of loss of the control plasmids (pEGFP-C1 and pd1EGFP-N1), which contained neither replication origin nor segregation element, this rate is still significantly lower. The rate of loss of plasmids containing PyV minimal core origin and FR-element (pFRG*) is also different from the previously published results of the rate of loss of several replicating plasmids that contained FR-element as stable maintenance factor, where the rate of loss was 2.1-7.8% (Wade-Martins et al., 1999) but it is very similar to the 15% rate of loss previously estimated for oriP containing plasmids (Hung et al., 2001).

The following examples are meant to be descriptive and by no mean limiting the various embodiments of the present invention.

EXAMPLE 1

Papillomavirus Type 1 E2 Protein and its Multimeric Binding Sites Activate Polyomavirus Core Origin Replication and Provide Segregation/Partitioning Function to the Origin Plasmid The BPV-1 E2 protein is multifunctional protein, which is involved in transcriptional regulation, viral DNA replication and segregation. It has been shown that for stable episomal replication of the BPV-1 E1 and E2 proteins, and MME element, which comprises multimeric E2 protein binding sites, are required.

It has been demonstrated that E2 protein can activate polyomavirus core origin transient replication in vivo in E2 multimeric binding site dependent fashion (Nilsson, 1991). There is however no suggestion nor evidence in the prior art of the BPV-1 E2 binding sites in the hybrid mouse polyomavirus origin being able in addition to the activation of the initiation of replication, also to provide the long-term maintenance function to the polyomavirus replicator in the cells expressing large T antigen and E2 protein.

FIG. 1 schematically shows the PyV hybrid origins constructed for this study. First group of plasmids includes the origin constructs, which include PyV wild-type origin and in addition one, five or ten E2 binding sites cloned in pUC19 plasmid (FIG. 1B). Second group of plasmids includes the origin constructs, where PyV enhancer element is removed (ori core) and one, five or ten E2 binding sites are added in the pUC 19 plasmid (FIG. 1C). Third group of plasmids (FIG. 1D) comprises origin-constructs together with eukaryotic selection cassette, such as the neomycin resistance gene, which makes possible to select for the plasmid positive transfected cells in stable maintenance assays (Materials and Methods).

Replication of the PyV origin requires large T antigen (LT) as the only viral replication factor—all other components are derived from the host cell. LT is an origin recognition factor, DNA helicase and thus directly participates in initiation and elongation of the replication of the viral origin. We constructed mouse cell lines expressing large T antigen and the BPV-1 E2 protein using the cell line COP5, which constitutively produces large T antigen from the integrated replication defective mutant of the polyomavirus genome. The eukaryotic selection marker containing vectors pBabeNeoE2 or pBabePuro were linearized and concatemerized at high concentrations with linear E2 expression plasmid (pCGE2). Ligation mixture was purified and transfected by electroporation into COP5 cells (Materials and Methods). Individual colonies were allowed to expand in the presence of selection (puromycin or G418), PyV LT and BPV-1 E2 positive double expression cell lines were identified and characterized. The cell lines expressing E2 protein at the highest level were used in further assays (referred to as COP5/E2/Puro or COP5/E2/Neo, selected for puromycin or G418 selection markers, respectively). The same approach was used for construction of cell lines, which express mutant forms of the E2 proteins, E39A and R68A (referred to as COP5/E39/Puro and COP5/R68/Puro). As described earlier, both these mutants are at least partially functional in E2 binding site dependent transcriptional activation and initiation of the BPV-1 origin replication as well as in activation of initiation of PyV core origin replication, however, they fail to support segregation/partitioning of the MME plasmids (Abroi et al. 2004). Expression of the E2 and E2 mutant proteins in the cell lines was verified using Western blot analysis (FIG. 2B). The cell lines expressing E2 or E2 mutants were grown for five months without G418 or puromycin selective pressure. The expression of the E2 proteins was maintained at detectable level for prolonged period without selection, which is essential requirement for study of the maintenance of the episomal plasmids.

Figure 3:
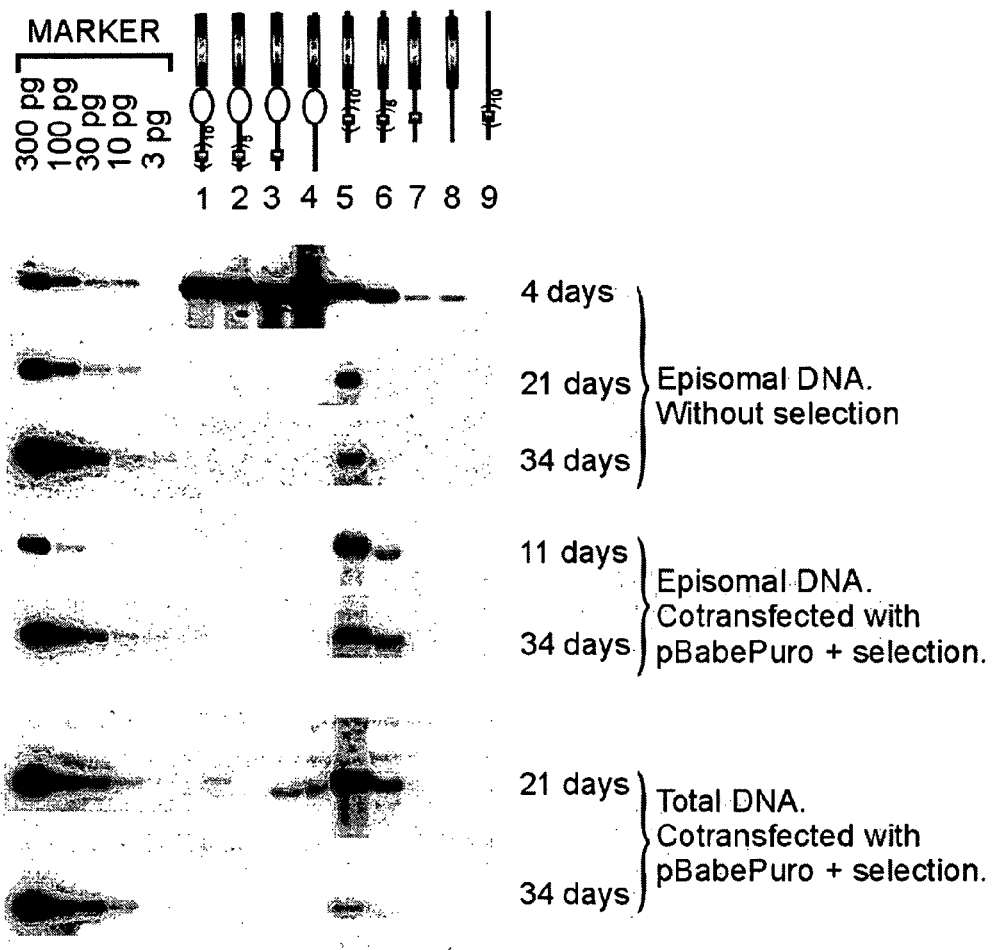
FIG. 3. Southern blot analysis. BPV-1 E2 protein and its binding sites are required for extended maintenance of PyV origin plasmids. (A) Transient and stable replication properties of PyV chimeric plasmids in wild-type E2 protein expressing cell line COP5E2/Neo. Episomal or total DNA was extracted from cells 4, 11, 21 and 34 days after transfection. For selecting PyV origin containing cells from the total population, cotransfection with linearized vector pBabePuro and puromycin selection were used. Purified DNA was digested with restriction endonucleases HindIII and DpnI. Filters were probed with radiolabeled PyV core origin and 10 E2 binding sites containing plasmid. 3 to 300 picograms of linear PyV core origin and 10 E2 binding sites containing plasmid was used as a marker. Transfected constructs are schematically represented above the figure (lines 1-9, see also FIG. 1 for explanation). (B) LT protein alone is not sufficient to provide maintenance function to PyV origin containing plasmids. 4 and 19 days after transfection low-molecular weight DNA was extracted and digested with restriction endonucleases HindIII and DpnI. Filters were probed with radiolabeled PyV core origin and 10 E2 binding sites containing plasmid. 1 to 300 picograms of linear PyV core origin and 10 E2 binding sites containing plasmid was used as a marker. Transfected constructs are schematically represented on the top of the figure (lines 1-9, see also FIG. 1 for explanation).
Figure 3:
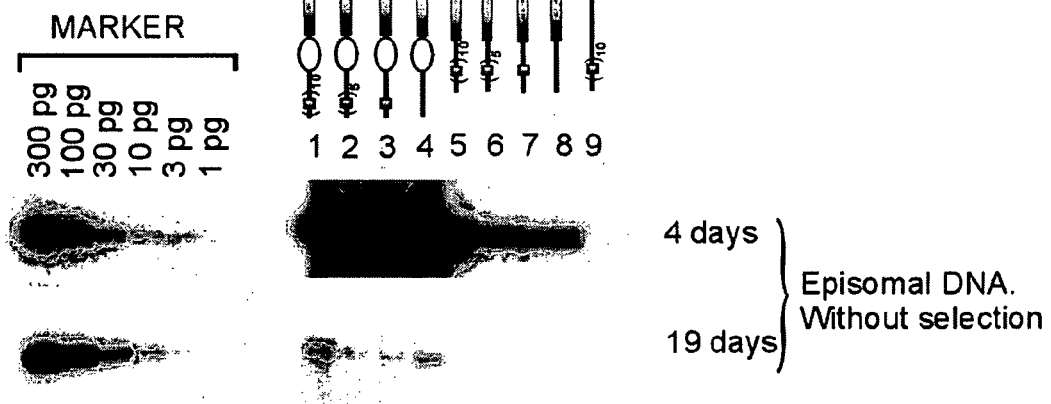

The constructed cell lines were used in further experiments to study the effect of the BPV-1 E2 protein and E2 binding sites on initiation of replication and maintenance of the constructed plasmids. At first, we examined the chimeric origins, comprising of the PyV wild type (wt) origin (FIG. 1B) or the core origin (FIG. 1C) linked to different number of E2 binding sites in cell lines COP5/E2/Neo (expressing constitutively PyV LT and BPV-1 E2) or COP5 (expressing constitutively PyV LT), respectively. 96 hours after transfection strong replication signals of wt origin plasmids were detected in both cell lines (FIGS. 3A and B, 4 days time points, lanes 1-4). The added E2 protein binding sites had rather inhibitory effect on the replication of the wt PyV origin. However, the E2 protein dependent activation of replication was clearly detected in the cases where PyV enhancerless core origin (SEQ ID NO:2) was linked with different number of E2 binding sites (SEQ ID NO:1) with spacers (SEQ ID NO:6 and 7). Addition of one E2 binding site had no effect on the initiation of replication of the core origin, however, addition five or ten E2 binding sites activated core origin replication to almost wild type origin replication level in the E2 protein dependent fashion (compare FIGS. 3A and 3B, lanes 5-9). In the COP5 cell line lacking E2 protein, the replication enhancer function of the E2 binding sites to the core origin cannot be detected (FIG. 3B). The result shows that the replication of PyV core origin can be activated by BPV 1 E2 and its binding sites.

We further studied the stable episomal maintenance of different PyV origin containing constructs in two settings. First, without any selection of the transfected cells and second, after cotransfection of the origin plasmids together with pBabePuro selection marker allowing selection for the transfected cells (Materials and Methods). The episomal persistence of the PyV origin containing plasmids was analyzed by Southern blotting. Wild type origin plasmids were lost from the cells under selective and non-selective conditions very fast in COP5E2/Neo and COP5 cells (FIGS. 3A and B). However, the hybrid origins comprising the core origin and five or ten E2 binding sites were capable of long-term persistence (11 and 34 days, at least 27 doublings) in the COP5E2/Neo cells as analyzed by episomal DNA extraction or analysis of total DNA from the transfected cells. Without selection after 21 and 34 days the only maintained origin construct was the hybrid of the core origin together with 10 E2 binding sites (FIG. 3A, 21 and 34 days time points without selection, lane 5). For PyV origin with five E2 binding sites a weak replication signal was detected at longer exposure (data not shown). We estimated the average copy-number of the episomal plasmids in the culture using total DNA Southern blot (FIG. 3A total DNA time points). Importantly, the plasmid with 5 and 10 E2 binding sites had in average 5 and 17 copies per cell after 34 days, respectively. This data indicate that E2 and its binding sites can provide maintenance function for chimeric PyV origin constructs that are otherwise lost from the cell population during cell growth. Because of the high copy number in cells the system according to this disclosure can be used for an efficient transient expression system.

Figure 4:
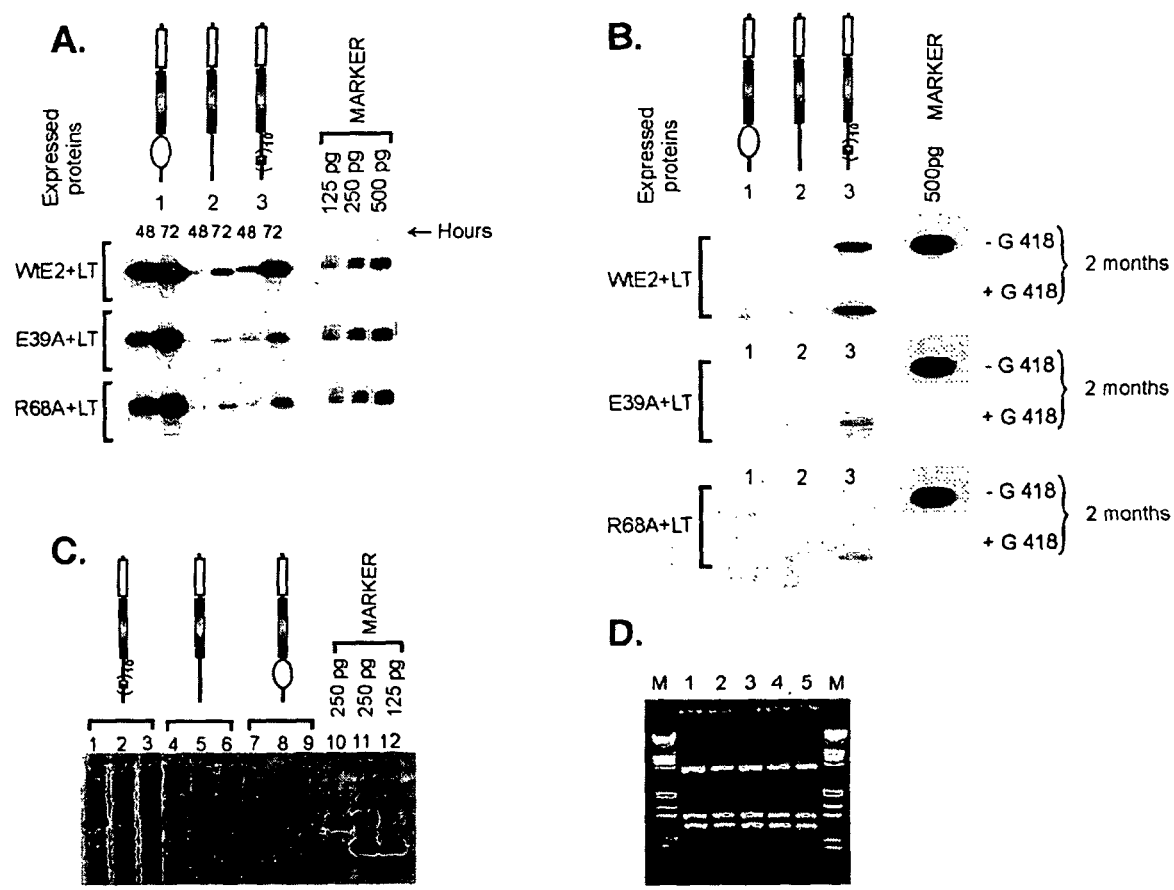
FIG. 4. PyV core origin in conjunction with MME is stably maintained without plasmid rearrangements. (A) Transient replication of neomycin selection cassette containing plasmids in cell lines expressing LT and wt E2 or its mutant forms E39A or R68A. Low-molecular-weight DNA was extracted 48 and 72 hours after transfection and digested with the single-cutting enzyme HindIII and with DpnI, which digests bacterially methylated unreplicated input DNA, and was analyzed by Southern blot (lanes 1-3). Transfected plasmids are schematically represented on the top of the figure (see also FIG. 1D). Marker lanes contain 125, 250 or 500 pg of linearized plasmid, which contains PyV core origin, 10 E2 BS and neomycin selection cassette. (B) E2 chromatin attachment function is required to provide the stable maintenance for PyV core origin in conjunction with MME. Cell lines expressing LT, wt E2 or mutant E2 proteins R68A or E39A were transfected with constructs which are schematically indicated on the top of the figure. After transfection cells were grown in the presence (+) or absence (−) of geneticine and analysed for stable replication (lanes 1-3). Low molecular weight DNA was extracted 2 months after transfection and digested with the single-cutting enzyme HindIII and with DpnI and analysed by Southern blot. 500 pg of linearized plasmid, which contains PyV core origin, 10 E2 BS and geneticine selection cassette is used as marker. (C) State of PyV origin containing plasmids. LT- and wt E2-expressing cells were transfected with plasmids indicated schematically on the top of the figure. After 2 months of growing cells in the presence of geneticine total DNA was extracted and analysed (2 µg) by linearizing enzyme HindIII (lanes 1, 4 and 7) and non-cutter enzyme EspI (lanes 3, 6 and 9). Uncut samples are represented in lanes 2, 5 and 8. The plasmid containing PyV core origin, 10 E2 BS and geneticine selection cassette is used as marker and is represented as 250 ng of linearized form (lane 10) and 250 pg or 125 pg of uncut forms (lanes 11 and 12). (D) Plasmid rescue analysis of COP5E2/Puro cell line. 5 months after transfecting plasmid containing 10 E2 BS, PyV core origin and geneticine selection cassette to COPE2/Puro cell line, total DNA was extracted and processed for plasmid rescue assay as described previously by Mannik et al. 2003. Rescued plasmids were analyzed with restriction endonuclease BglII. In the lane 1, the pattern of input plasmid is represented. In the lanes 2-5, the patterns of rescued plasmids are represented from 4 separate colonies. Lanes 'M' contain marker LambdaDNA/EcoRI+HindIII (Fermentas, Lithuania).

Importantly, when the papillomavirus segregation/partitioning element is linked to the PyV wt origin (short term replication signals on FIG. 3A, 4 days time points, lanes 1-4) these replicons are not able to survive despite of their intensive replication initiation (FIG. 3A, lanes 1-4). This could be due to the too effective enhancer activities resulting in over-replication of the origin plasmid leading to the cell death. Inspection of the transfected culture indicated that indeed the wt PyV origin plasmids induced extensive cell death at the later time points.

EXAMPLE 2

Replication of the Origin Plasmids Carrying Episomal Selection Marker

COP5E2/Puro cells were transfected with three different constructs carrying geneticine selection marker (FIG. 1D). The eukaryotic selection cassette for neomycin enables selection for the cells carrying episomal plasmid in transfected cells in the presence of G418. Transient transfection of COP5E2/Puro with neomycin-reporter plasmids resulted in strong replication signal for wt origin construct (FIG. 4A, time points at 48 and 72 hours, lane 1) compared to much lower replication signal for core origin construct (FIG. 4A, 48 and 72 hrs time points, lane 2). The addition of ten E2 binding sites to core origin increased the transient replication signal to the level comparable to the wt origin (FIG. 4A, 48 and 72 hours time points, lane 3). The transfected cells were grown in the medium containing G418 selection, after which they were kept through series of cell divisions with and without selection. After 2 and 5 months of cultivation these cell lines were analyzed for plasmid stable maintenance functions with Southern blotting and with origin probe for hybridization. Ten E2 binding sites containing reporter plasmid could establish the extrachromosomal maintenance of autonomous episomes in E2-positive cell population after two months and even after five months (FIG. 4B, lanes 3, analysis after two months). Removal of selection could not change the detection of the replication signal in clonal cell lines (FIG. 4B, lanes 3, two month time point). FIG. 4D shows plasmid rescue analysis (cf. Materials and Methods) of COP5E2/Puro cell line and proves that after 5 months from transfection no rearrangements of plasmids were detected. Markedly, we found that addition of Minichromosome Maintenance Element from the BPV-1 to the core origin of PyV gives an unusual feature to PyV replicator—the feature of long term replication of episome in cell lines, which express LT and E2 proteins.

Figure 2:
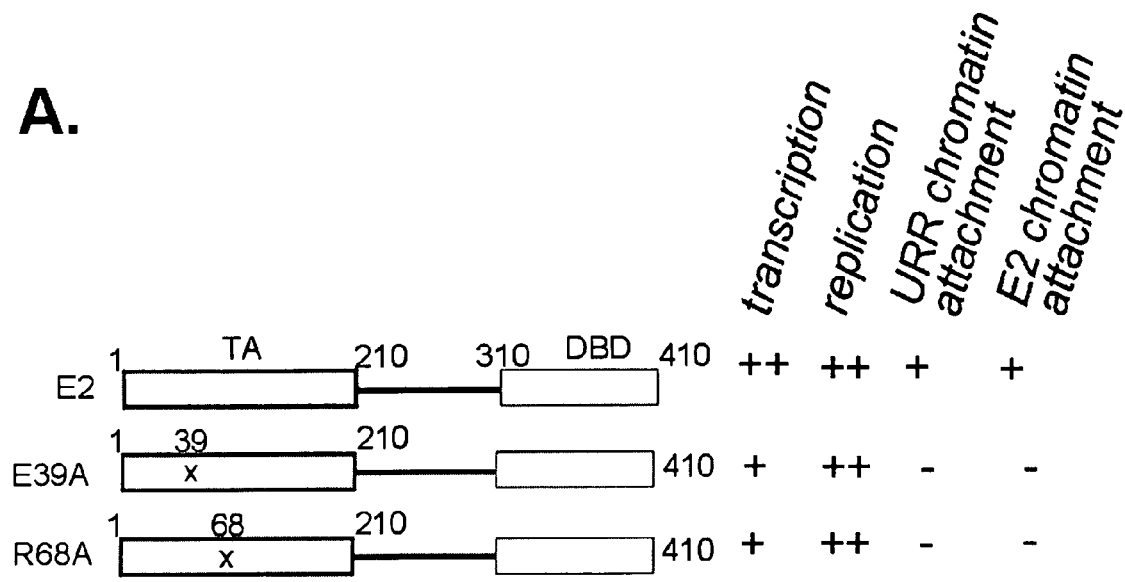
FIG. 2. (A) Schematic representations of designed E2 point mutations and their properties in BPV-1 life cycle, which are described in more details by Abroi et al. 2004. (B) Western blot analysis of the expression of wild-type (lane 2 and 3) and mutant E2 proteins (lane 4 and 5) in constructed COP5 derivate cell lines. Cells from a semiconfluent 60-mm diameter dishes were lysed in 100 µl of Laemmli sample buffer and ⅓ of cell lysate was loaded in each lane. Negative control lysate was prepared from COP5 cells (lane 6). The purified E2 protein expressed in bacteria was used as positive control (lane 1). Comparisons of the expression levels and estimations of the intactness of wild-type and mutant E2 protein were conducted by using 3F12 antibody (Kurg et al., 1999).
Figure 2:
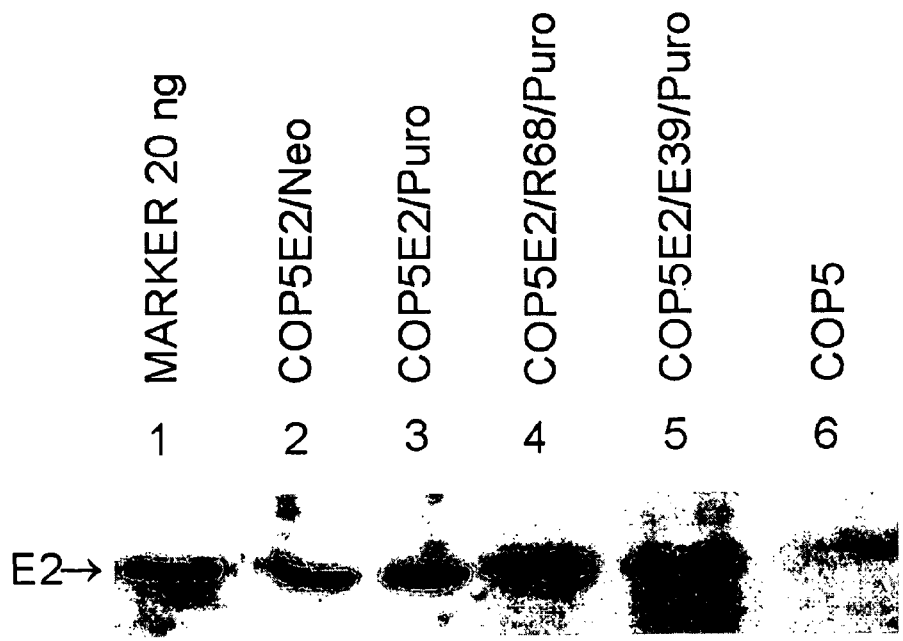
Figure 5:
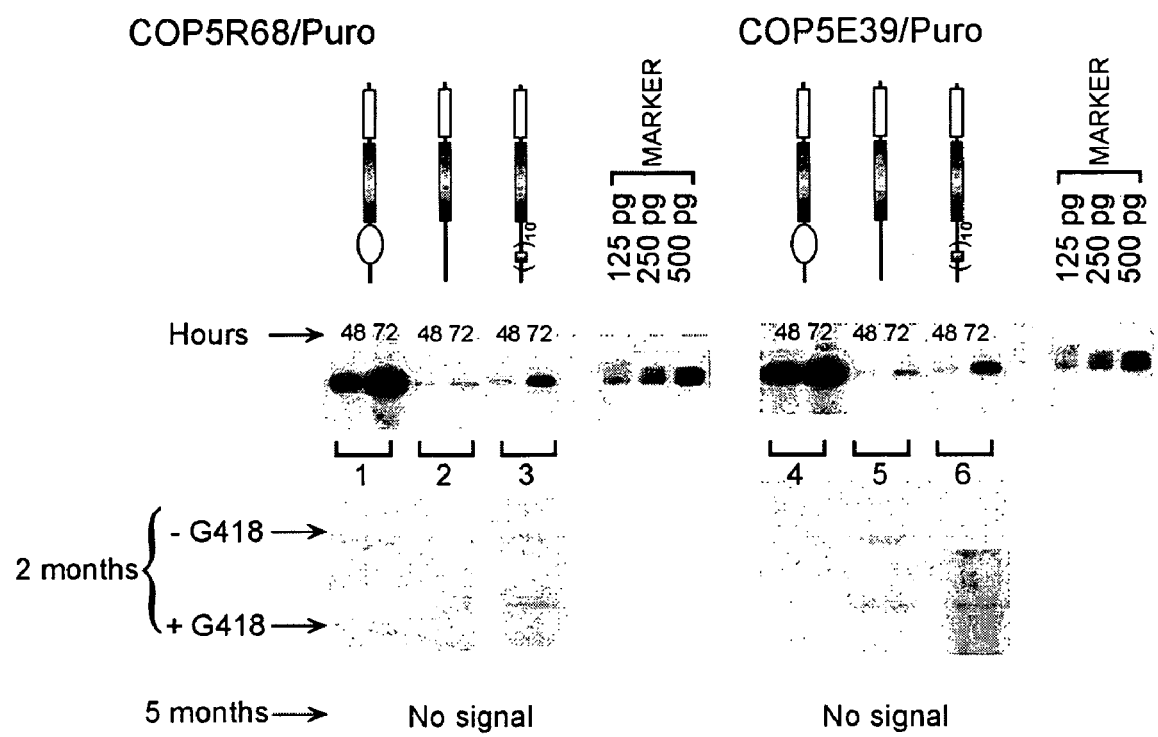
FIG. 5. E2 chromatin attachment function is required to provide extended maintenance for PyV core origin in conjunction with MME. Cell lines expressing mutant E2 proteins R68A and E39A were transfected with constructs which are schematically indicated on the top of the figure. After transfection cell were growing in the presence (+) or absence (−) of G418 and analysed for transient (lanes 1-3, 48 and 72 hours timepoints in COP5R68/Puro cell line; lanes 4-6, 48 and 72 hours timepoints in COP5E39/Puro cell line) and stable replication (lanes 1-3, 2 and 5 months timepoints with and without G418 selection in COP5R68/Puro cell line; lanes 4-6, 2 and 5 months timepoints with and without G418 selection in COP5E39/Puro cell line). Marker lanes contain 125, 250 or 500 pg of linearized plasmid, which contains PyV core origin, 10 E2 binding sites and neomycin selection cassette.

We compared the extended episomal maintenance of the hybrid origins in the cell lines expressing wild type E2 or mutant forms of E2 carrying the alanine substitutions of the conserved charged residues in N-terminal domain. These mutants have been previously characterized in papillomavirus replication, transactivation, sequence-specific DNA binding and partitioning assays. E2 mutants E39A and R68A (scheme A on FIG. 2) are inactive in the chromatin attachment functions and failed to mediate the segregation/partitioning of the BPV1 URR reporter plasmids, but were still active in initiation of transient replication and in transcription, where their relative activity was comparable to wild type E2. Puromycin resistance clones of COP5 were selected for LT and BPV-1 E2 mutant forms R68A or E39A. Positive cell lines were cloned and characterized (protein expression on FIG. 2B), the best expressing cell lines were selected for subsequent assays. We used the neomycin-constructs (FIG. 1D) for short and long-term replication assays in double-expression mouse cell lines expressing the two mutant forms of E2. Both expressed E2 mutant forms R68A and E39A activated PyV core origin replication in E2 binding site dependent fashion (FIG. 4A lane 3 and FIG. 5, lane 3 and 6, 48 and 72 hours time points). These results show that E2 mutant forms R68A and E39A have similar effect to replication activation as wt E2 protein. The transfected cells were grown in the media with and without neomycin selection for time-period up to 5 months. After 2 months there was very weak replication signals observed even with neomycin selection (FIG. 4B, lanes 1-3, two months time points). After 5 months of cultivation there were no episomal replication signals in cell lines expressing mutant forms of E2 (FIG. 5). Same results as in cell lines expressing mutant E2 proteins R68A and E39A were achieved by using cell lines which express hybrid protein variations, VP16/E2 and p53/E2 (FIG. 2A) where the whole transactivation domain of the E2 protein is replaced with respective activation domain from VP15 or p53 protein, respectively (data not shown). The persistence of expression of the viral proteins by western blotting after 5 months of growth is shown in FIG. 2B. As conclusion the overall structural integrity as well as the intactness of domains of E2 is required for efficient segregation, because only the wt E2 could provide stable maintenance functions to PyV core origin together with the PyV LT in trans. On the other hand these results showed that chromatin attachment function of E2 protein is required to ensure stable maintenance of chimeric PyV origin.

EXAMPLE 3

Episomal State of Chimeric Origins was Maintained Without Rearrangements

Figure 6:
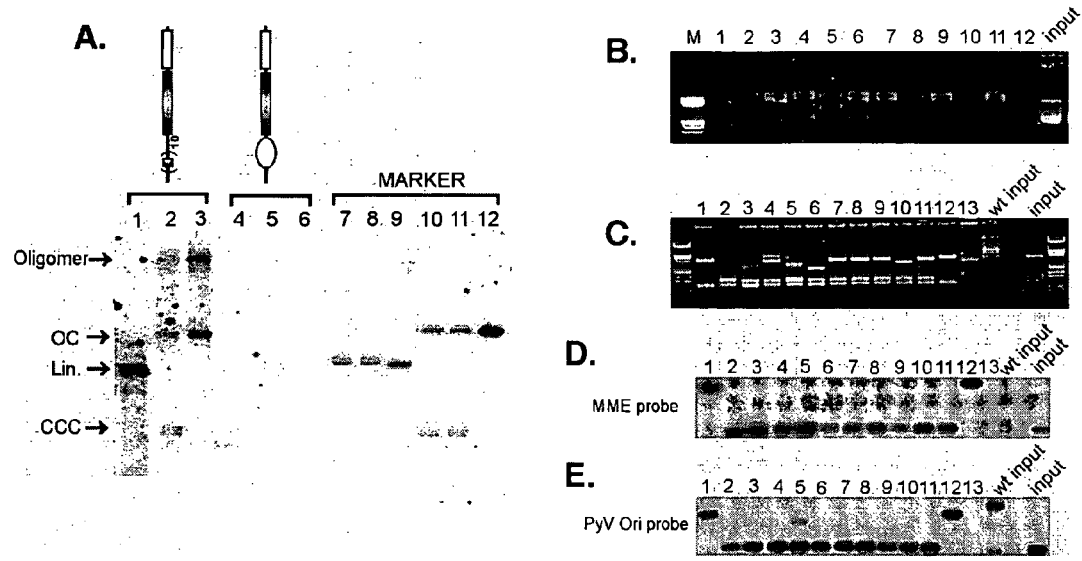
FIG. 6. PyV core origin in conjunction with MME is stably maintained as episome. (A) LT and wt E2 expressing cells were transfected with plasmids indicated schematically above the figure. After 2 months of growing cells without geneticine episomal DNA was extracted and analysed by linearizing enzyme HindIII (lanes 1 and 4), with non-cutter NdeI (lanes 2 and 5) and plasmid nicking enzyme Nb.Bpu10I together with non-cutter enzyme NdeI (lanes 3 and 6). Plasmid containing PyV core origin, 10 E2 BS and geneticine selection cassette was used as marker (100 pg on each lane, lanes 7-12) and is represented as: linearized form (lane 7), circular form digested with linearizing enzyme HindIII and nicking enzyme Nb.Bpu10I (lane 8), circular form digested with linearizing enzyme HindIII in presence of COP5E2/Puro episomal DNA (lane 9), non-cut forms (lanes 10), circular forms digested with non-cutter NdeI (lane 11) and circular form digested with non-cutter NdeI and nicking enzyme Nb.Bpu10I (lane 12). Covalently closed circular (CCC), linear (Lin.), open circular (OC) and oligomerized forms of DNA are indicated with arrows. All restriction reaction contained 2 units of DpnI. (B, C, D, E) Plasmid rescue analysis of COP5E2/Puro cell line. 2 months after transfecting plasmid containing 10 E2 BS, PyV core origin and geneticine selection cassette to COPE2/Puro cell line, total DNA was extracted. 2 µg of uncut total DNA was processed for plasmid rescue assay as described in material and methods. (B) In the lanes 1-12, the uncut rescued plasmids are represented from 12 separate colonies. Lane 'M' contains marker LambdaDNA/HindIII (Fermentas, Lithuania). (C) Analysis of rescued plasmids with endonuclease BglI. (lanes 1-12). Lane 13 represents BglI digestion of DNA extracted from colony on control plate (plasmid rescue assay with uncut total DNA from cells which carry reporter plasmid with wt PyV origin and geneticine selection cassette). (D) BglI digestion fragments of rescued plasmids analyzed by Southern blot with MME specific probe (lanes 1-13). (E) BglI digestion fragments of rescued plasmids analyzed by southern blot with PyV origin specific probe (lanes 1-13). Input or wt input lanes contain plasmid with PyV core origin, 10 E2 BS and geneticine selection cassette or plasmid with PyV wt origin and geneticine selection cassette, respectively.

A high mutation frequency, especially recombination, is often associated with replication from the papillomavirus and polyomavirus origin based vector systems. Extrachromosomal low weight DNA, used in our replication assays was extracted using the Hirt procedure. In the double expression cell line COP5/E2/Puro the hybrid origin-derived vectors persist in the episomal state was analyzed in FIGS. 4C and 6A. Linearized DNA fragments showed only one very discrete unit-size band as compared to the marker (FIG. 4C, lanes 1 and 10 and FIG. 6A, compare lanes 1 and 9). Comparison of the uncut sample and the sample digested with non-cutter (enzyme with no restriction sites for plasmid DNA), gave the same patterns (4C, compare lanes 2 and 3, also 5 and 6) where open circular (OC) and covalently closed circular (CCC) forms can be detected (FIG. 6A lanes 2, 10 and 11) indicating that this was not the integrated material (before the capillar blotting the gel was analyzed with EtBr staining, showing the complete restriction of used enzymes). However, the uncut plasmid marker (FIG. 4C, lanes 11 and 12) is not matching exactly with uncut DNA of analyzed samples, which move more slowly (FIGS. 4A and 6A lanes 2 and 3). Thus we suggest that these are the oligomerizied episomes or cateanates of the episomes as it has been demonstrated for BPV-1 viral genomes in several cell lines.

The presence of episomal DNA was also confirmed by plasmid rescue into *E. coli* from the uncut total DNA of hybrid replicon of polyoma core origin and 10 E2 binding sites grown in double expressing cell line of wt E2 and LT. The intact, unarranged DNA forms could be detected with different restriction enzyme combinations (FIG. 4C). Analysis of uncut rescued plasmids showed an oligomerized pattern compared to input DNA (FIG. 6B). Restriction analysis of rescued plasmids by endonuclease BglI showed that, compared to input DNA some rearrangements in the plasmid backbone can be observed (FIG. 6C, lanes 1 to 3, 5, 6, 10 and 12). Thus some cells carried plasmids with rearrangements. In addition, intact unarranged DNA forms were also detected (FIG. 6C, lanes 4, 7 to 9, and 11). To confirm that rescued plasmids still contain the PyV origin and MME, we analyzed the BglI digestion pattern by Southern blot analysis with an MME- or PyV-specific probe (FIGS. 6D and E, respectively). Southern blot analysis showed that all rescued reporter plasmids contained the MME and PyV origin fragment (FIGS. 4D and 6D and E). A plasmid rescue assay with total DNA (total DNA was extracted from cells whose episomal DNA is analyzed in FIG. 6A, lanes 4 to 6) from cells carrying the reporter plasmid with the wt PyV origin revealed only one colony, which was analyzed for the existence of the MME or PyV origin fragment (FIGS. 6D and E, lanes 13). Southern blot analysis indicated that plasmid DNA from this colony did not contain MME or the PyV origin (FIGS. 6D and E, compare lane 13 with lanes wt input and input). Removal of selective pressure did not affect the episomal status of the derived molecules. The results of these experiments strongly suggest that the cell lines we used carry the input vectors as extrachromosomal elements.

EXAMPLE 4

Measurement of the Episomal Plasmid Loss Using Flow Cytometry Analysis

Figure 7:
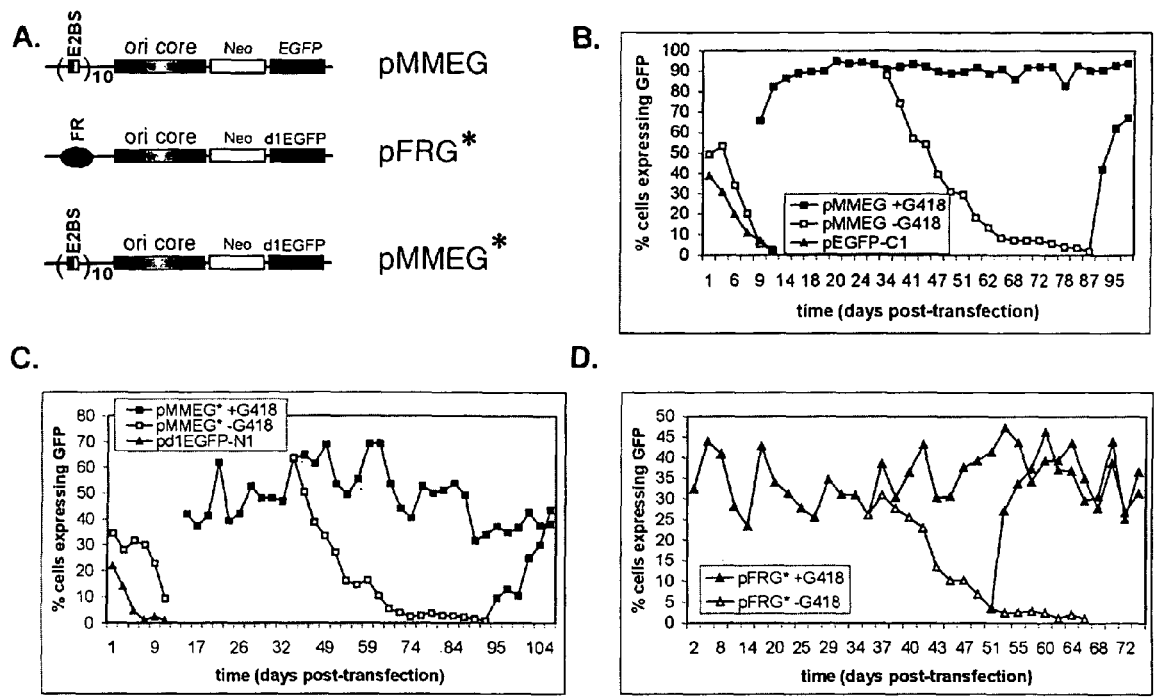
FIG. 7. Schematic representation of PyV hybrid origin constructs used in flow cytometry analysis (A). Time course of long-term EGFP (B) or short-term d1EGFP (C,D) expression in the presence or absence of G418 selection for various cell lines. COP5E2/PuroMMEG (B); COP5E2/PuroMMEG* (C); COP5EBNA1/PuroFRG* cell line (D).
Figure 9:
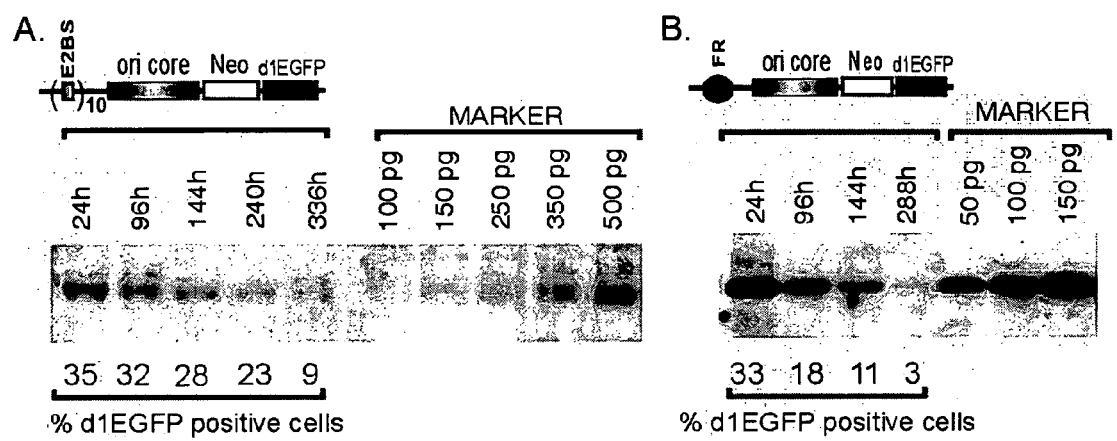
FIG. 9. Southern blot analysis of the COP5E2/PuroMMEG* cell line (A) and COP5EBNA/PuroFRG* (B) cell lines after removal of the G418 selection. At the indicated times after removal of the selection total DNA was extracted from cells and double-digested with DpnI and MluI (linearizes pMMEG* and pFRG* plasmids). A. Lanes 1-5: 10 μg of total DNA from COP5E2/PuroMMEG* cell line (24-336 h time point), lanes 6-10 marker plasmid pMMEG* (100-500 pg) linearized with MluI. B. Lanes 1-4: 3 μg of total DNA from COP5EBNA/PuroFRG* cell line (24-228 h time point), lanes 5-7 marker plasmid pFRG* (50-150 pg) linearized with MluI. At the same time the decrease in the percentage of d1EGFP expressing cells was monitored with FACS (presented under Southern blot analysis).

Maintenance of the plasmids containing PyV core origin, MME, selection marker (geneticine resistance) and green fluorescent protein marker (either long half-life EGFP or short half-life d1EGFP) was analysed by flow cytometry. Transfection of these plasmids (FIG. 7) into the COP5E2/Puro cell line resulted in efficient transient replication of both of these plasmids, which could be detected by Southern blot analysis (data not shown), as well as measured following EGFP fluorescence. Two different variants of EGFP protein marker were used comparatively to avoid potential problems of by-fluorescence of long half-life EGFP in the case of short-term experiments. Transfected cells were grown in continuous culture in the presence or absence of geneticine for up to 96 days. The cells were passaged every second day, assuring active growth. During each passage 100 000-200 000 cells were taken for analysis and the proportion of EGFP-positive cells was measured by flow cytometry. The percentage of cells expressing EGFP above background (COP5E2/Puro) was calculated for each transfected cell culture at each timepoint. Without geneticine selection the number of EGFP fluorescent cells decreased quite rapidly. Eleven days after transfection without selection few EGFP positive cells could be detected using FACS (fluorescence activated cell sorter) analysis compared to the initial approximately 50% of the EGFP positive cells in the culture (FIGS. 7B and C). Selection of the COP5E2/Puro cells transfected with the plasmid carrying neo-selection marker resulted in the cell culture, which had nearly 100% EGFP positive cells in the case of plasmid expressing long half-life EGFP, and approximately 50%, when plasmid was expressing short half-life d1EGFP (FIGS. 7B and C). Markedly, the percentage of EGFP-positive cells stayed constant for over more that twenty cell generations clearly proving that these cells are capable of long term maintenance of episomal genetic elements that contain PyV core origin and MME. Furthermore, the result shows that the system can be used to obtain long term expression of gene products, such as proteins or RNA. Accroding to this embodiment by providing a selection marker in the vector enables a possibility to develop stable cell lines. However, the results show that expression of gene products can be continued also for a significant time without a selection marker. This may become an important application in situations where use of antibiotics is not allowed. When the geneticine selection was removed the percentage of EGFP-positive cells decreased from 90% to approximately 1% in 55 days (from 64% to 2.4% in the case of d1EGFP in 37 days). In the case of integration of the episome the percentage of the EGFP-fluorescent cells should remain constant even when the selection is removed (Wade-Martins et al., 1999). To exclude the possibility that the loss of EGFP fluorescence is due to inactivation of the promoter of EGFP or the uneven distribution of the plasmid, we also analysed the DNA content in the cells. As presented in FIG. 9 the loss of the episomal plasmid DNA from the cells grown without the geneticine selection correlates with the flow cytometry analysis. In order to study the kinetics of loss of the episomes, the rate of loss for each episomal construct during the non-selective conditions was calculated. The results are provided in FIG. 8. Two control plasmids— pEGFP-C1 and pd1EGFP-N1 (control plasmids from Clontech lacking replication origin and MME) were used in the flow cytometry study to provide the comparison of the rate of loss of the episomes in COP5E2/Puro cell line. The rates of loss of these control plasmids in transfection of COP5E2/ Puro cell line are also shown in FIG. 8. After growing COP5E2/PuroMMEG and COP5E2/PuroMMEG* cells without selection for 55 days and COP5E2/PuroMMEG* cells for 37 days, 1% of the cells still contained the episome similarly as indicated by the flow cytometry analysis. When the geneticine selection on COP5E2/Puro (transfected either with pMMEG or pMMEG* plasmid) cell line was restored at this point, the proportion of EGFP expressing cells increased back to the initial level (FIGS. 7B and C).

EXAMPLE 5

Comparison of BPV-1 MME and EBV FR Element in Providing Segregation/Partitioning Function to the PyV Core Origin Plasmids Similar cell lines based on the COP5 cell line expressing PyV LT and EBV EBNA1 were constructed as well as the plasmids carrying EBV FR-element instead of BPV1 MME were made. The flow cytometry analysis was conducted in the COP5EBNA1/Puro cell line with plasmid containing PyV core origin, FR-element, selection marker (geneticine resistance) and green fluorescent protein marker (short half-life d1EGFP) (pFRG*). In this case the replication function of the plasmid is provided by PyV core origin and LT protein and the segregation/partitioning function is provided by FR-element and EBNA1 protein of the EBV. The results are similar to the flow cytomery analysis with plasmids pMMEG and pMMEG* in COP5E2/Puro cell line. Transfected cells were grown in continuous culture in the presence or absence of geneticine for up to 75 days. Selection of the transfected COP5EBNA1/PuroFRG* for geneticine resulted in the cell culture, which had approximately 40% d1EGFP positive cells (FIG. 7 D). When the geneticine selection was removed the percentage of d1EGFP-positive cells decreased from 40% to 1% in 30 days. When the geneticine selection on COP5E2/PuropFRG* cell line was restored at this point, the proportion of EGFP expressing cells increased back to the initial level (FIG. 7D). These results show that episomal persistence of the plasmid occurs with certain efficiency, which is different from 100%. Clearly also, EBNA1/FR and E2/MME elements confer comparablee segregation/partitioning funcitions fo the PyV core origin reporter plamsids in the cell models.

To exclude the possibility that hte loss of EGFP fluorescence is due to inactivation of the promoter of EGFP, we also analyzed the DNA content in the cells. After removal of geneticin selection total DNA was extracted from cells and digested with MluI (linearizes pMMEG* and pFRG* plsamids) and DpnI. Equal amonts of total DNA were then anlayzed using Southern blotting with a radioactively labelled probe against the pMMEG* or pFRG* plasmid. As presented in FIG. 8 the loss of the episomal plasmid DNA from the cells grown without Geneticin selection correlates with the flow cytometry analysis. On the other hand, these resultss indicate that EGFP fluorescence was indeed measured from plasmids which exists in the episomal state. In the cse of pasmid integration the hybridization signals remained constant.

EXAMPLE 6

Cell Lines Transfected with Hybrid Expression Vector Containing a Gene of Interest are Able to Express the Gene Product We used luciferase gene as a gene of interest (reporter gene) and inserted it into the vector with which the cell lines were transfected.

Figure 10:
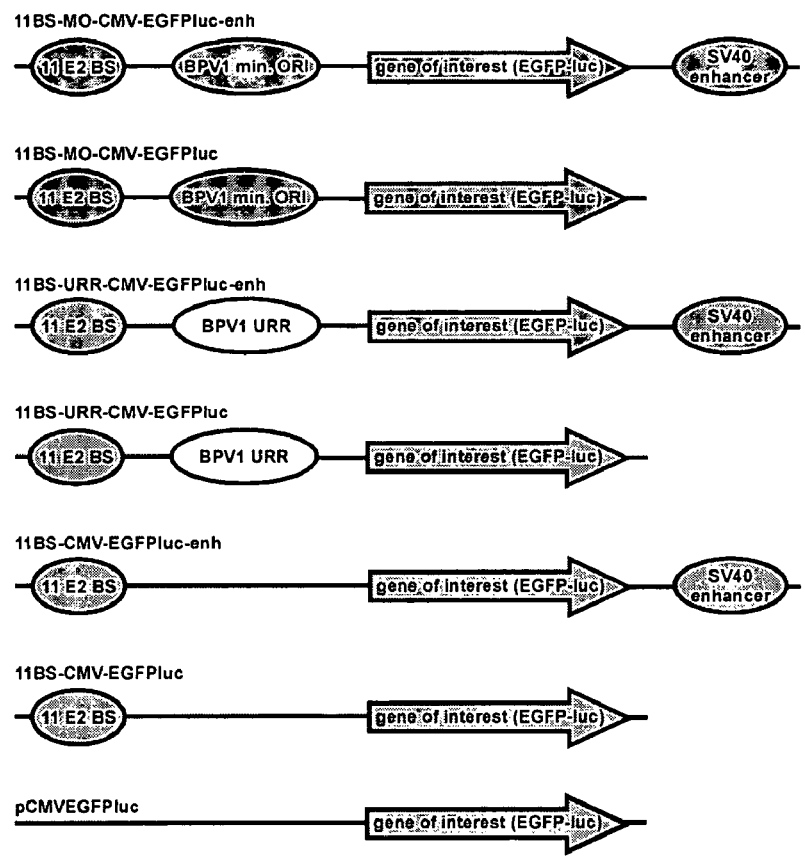
FIG. 10. Expression of luciferase in CHO 4.15 E2 cell line. Schematic representation of recombinant plasmid constructs used in expression analysis (A). Time course of luciferase expression analysed 2 days, 5 days and 7 days after transfection by electroporation of CHO 4.15 E2 cells (B).
Figure 10:
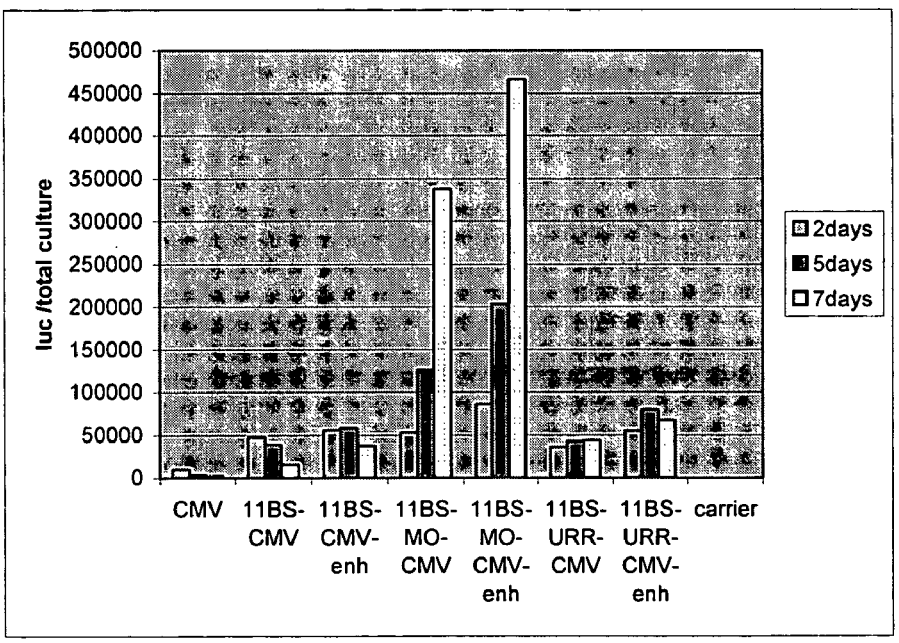

Cell lines based on the CHO cell line expressing BPV E1, BPV E2, were constructed as well as the plasmids carrying HPV 11 E2 BS, CMV promoter, BPV MO, BPV URR, SV40 enhancer and recombinant EGFP-luciferase gene (FIG. 10, panel A)

The cells were transfected with respective expression vectors using electroporation. The aliquots of the transfected cells were analyzed for the luciferase activity 2 days, 5 days and 7 days after the transfection. The difference for expression (FIG. 10) indicates that the vectors differ in their capacity to produce the reporter more than an order of magnitude. The efficiency of expression of reporter gene is in favor of HPV E2 multimeric binding site and BPV MO carrying vectors 11 BS-MO-CMV-EGFP-luc and 11 BS-MO-CMV-EGPF-Luc-enh. The E2 binding site used in this example originated from HPV and has a nt sequence essentially as ACCGAAACGGT (SEQ ID NO: 9). In the vector the multiple binding sites are separated by spacers, that may be but are not limited to sequences according to SEQ ID NO:6 and SEQ ID NO:7.

Materials and Methods Used in the Examples

Plasmids. For constructing hybrid replicons (FIG. 1 groups B and D), containing PyV origin (wild-type or core origin), we used vector pUC19 as the basic backbone where we cloned 1, 5 or 10 head-to-head copies of high-affinity E2 binding site 9. PyV wt and core origin were amplified by PCR from vectors pmu1046/CAT and pmu1047/CAT using primers Py4963 (5'-AGGGAGCTACTCCTGATG-3') (SEQ ID NO:3) and Py174 (-CTACCACCACTCCGACTT-3') (SEQ ID NO:4). Amplified PyV origin fragments were digested with enzymes EheI and BclI and inserted between BamHI and HincII sites of pUC19 vector containing different number of BPV-1 E2 binding sites. The E2 binding site is preferably according to ACCGNNNNCGGT (SEQ ID No: 1) where N is any nucleotide. Preferably the sequence is according to SEQ ID NO:5 (ACCGTTGCCGGT). In the vector it exists together with spacers, such as GATCTGT (SEQ ID NO:6) and CG (SEQ ID NO:7) forming a repeated unit GATCTGT ACCNNNNNNGGT CG (SEQ ID NO:8).

Neomycin gene containing hybrid replicons (FIG. 1D) were established by replacing URR in plasmid pNeoBg140 with PyV wt origin, core origin or core origin with 10 E2 binding sites, which were amplified by PCR and digested with enzymes BamHI and Ecl136II and cloned into BamHI and HindIII sites in pNeoBg140.

Three types of the EGFP (green fluorescent protein) marker containing plasmids were designed. First, fragment comprised of PyV minimal origin (SEQ ID NO:2) and 10 E2 binding sites was added to the plasmid containing geneticine resistance marker (expressed from the simian virus 40 promoteer SV40). Then either EGFP or destabilized green fuorescent protein (d1EGFP) marker was added (named either pMMEG or pMMEG* plasmid, FIG. 7A). EGFP expression cassettes, which are under the control of the Cytomegalovirus immediate-early promoter (CMV), were taken either from pEGFP-C1 or pd1EGFP-N1 plasmids (Clontech). For the third plasmid, first Epstein-Barr virus (EBV) FR-element was added to pUC19 plasmid containig PyV core origin. Then the fragment containing PyV minimal coren origin and ten E2 binding sites from plasmid pMMEG* was replaced by fragment containing PyV minimal core origin and EBV FR-element (plasmid pFRG*, FIG. 7A Construction of Cell Lines.

For construction of cell lines, which express BPV-1 wt E2 protein and its mutant forms E39A and R68A, the vector pBabePuro was linearized using enzyme SalI and was ligated with equal amount of E2 expression vectors (pCGE2, pCGE2/R68, pCGE2/E39), which were linearized with XhoI endonuclease. 1 μg of ligated hybrid plasmids was electroporated into COP5 cell line. COP5 cell line is derived from mouse C127 cells (ATCC CRL-1804) and described in Tyndall et al. 1981. Electroporation experiments were preformed with a Bio-Rad Gene Pulser with capacitance and voltage settings of 975 μF and 220 V. For selection puromycin (2 μg/ml) was added. The expression of the proteins was analyzed by Western blot.

A cell line which expresses wt E2 and carries neomycine selection cassette was constructed by the same protocol described above, using vector pBabeNeo instead of pBabePuro.

A cell line expressing PyV T-antigens and EBV EBNA1 protein was generated as a result of transfection of the NotI linearized plasmid pBabePuro/EBNA1 (EBNA1 coding sequence inserted into EcorI/SalI sites in pBabePuro vector) into COP5 cell line and selection for puromycin (2 μg/ml). The expression of the proteins was analyzed by Western blot. The cell line was named COP5EBNA1/Puro.

In example 6 (FIG. 10) cell line CHO4.15 was used. This cell line is derived from CHO-K1 cell line (ATCC CCL 61) and described in Ustav 1993. CHO derived cell lines expressing EBV EBNA1, PyV LT, BPV E2 were constructed using the same method as used for construction of COP derived cell lines.

Cells and transfection. COP5 cells (Tyndall et al., 1981) and its derivatives COP5E2/Puro, COP5E2/Neo COP5R68/Puro, COP5E39/Puro, COP5EBNA1/Puro expressing polyomavirus T-antigens and BPV-1 wt E2 or its mutant forms or EBNA1 were grown in Iscove's modified Dulbecco's medium ("Difco") supplemented with 10% fetal calf serum.

For selection G418 (500 μg/ml) or puromycin (2 μg/ml) were added, depending on selection marker. Electroporation experiments were performed with a Bio-Rad Gene Pulser with capacitance and voltage settings of 975 μF and 220 V, respectively.

COP5E2/Puro cells transfected with neomycin-constructs were selected with G418 at 500 μg/ml. COP5E2/Neo cells co-transfected with pBabePuro (Morgenstern, J. P., and H. Land. 1990) were selected with puromycin at 2 μg/ml. After transfection with plasmids carrying geneticine resistance marker and GFP codeing sequence, COP5EBNA1/Puro cell line was grown in IMDM medium containing 500 μg/ml G418 (medium contained no puromycin).

Southern blot analysis. Total DNA was extracted from cells following standard protocol. Extraction of low-molecular-weight DNA from cells as well as analysis of origin constructs levels in both low molecular weight and total DNA preparation were performed as described previously (Ustav and Stenlund, 1991; Piirsoo and Ustav 1996). Specific probes were labeled with [$^{32}$P]dCTP by random-hexamer-primed synthesis using DecaLabel kit (Fermentas, Lithuania). Hybridizing species were visualized by autoradiography. Radioactive signals on the blots were quantified on PhosphorImager using ImageQuant software (Molecular Dynamics, Amersham Biosciences, UK).

Immunoprecipitation. Cells (1.5×10$^7$) were lysed with ice-cold 1% sodium dodecyl sulfate (SDS)-phosphate-buffered saline on ice, collected in a 15-mil tissue culture tube, and sonicated. From this step an aliquot for the Bradford assay was taken. SDS was diluted to 0.1% by adding ice-cold radio-immunoprecipitation assay (RIPA) buffer (50 mM Tris-HCl, pH 8.0, 150 mM NaCl, 1% NP-40, 0.5% dexycholate, 0.1 mM dithiotreitol (DDT), 0.5 mM phenylmethylsulfonyl fluoride, protease inhibitors). The insoluble fraction was sedimented by centrifugation at 5,000×g for 15 min. The soluble fraction was transferred to a new tube and incubated with 5H4, 3E8, 1'E4 and 3F12 antibodies over night at 4 C. Then protein G-Sepharose (Amersham Biosciences) was added and incubated for 1 h. Sepharose beads where washed three times with RIPA buffer and resuspended in SDS loading buffer and subjected to immunoblotting analysis with horse-radish peroxidase-conjugated eE11 (subclone of MAb 3F12 (antibody (Quattromed AS, Tartu, Estonia).

Immunoblotting. Total protein from the same number of cells lysed in standard loading buffer supplemented with 100 mM DDT was separated by electrophoresis on 8% polyacrylamide-SDS gel and transferred to Immobilon-P membrane (Millipore, USA). Antibody 1E4 (Kurg et al., 1999) was used to detect E2 proteins. Antibodies BM3167 and BM1083 (DPC Biermann) was used to detect EBNA1 protein. Peroxydase-conjugated goat-anti mouse antibody and the enhanced chemoluminescence detection kit (Amersham Biosciences) were used for subsequent developing of the blot, using a standard protocol provided by the supplier.

The plasmid rescue assay was performed for detection of the episomal state of the plasmid as described previously in Männik et al 2003. Two micrograms of uncut genomic DNA was electrotransformed in to *Escherichia coli* strain DH 10B. The electorcompetent cells were prepared and the transformations were performed using a Pulser apparatus and 2-mm electroporation cuvette (Bio-Rad Laboratoires, Hercules, Calif.) according to the manufacturer's instructions. The cells were recovered by centrifugation and were grown on medium containing ampiclillin at 100 μg/ml. Plasmid DNA from single colonies was purified and analyzed using restriction endonucleases.

Flow cytometry analysis. EGFP expression was analysed by flow cytometry using Becton-Dickinson FACSCalibur flow cytometer with associated CellQuest software. 100 000-200 000 signals were analysed from each sample. The threshold for autofluorescence was set to 99% of the signals from the mock-transfected control cells. All the signals above the threshold were considered to correspond to EGFP-positive cells. For calculating the episomal rates of loss in the FIG. 8, EGFP expression data was analyzed on days 0 and 12 (pEGFP-C1, pd1EGFP-N1), on days 0 and 55 for pMMEG, on days 0 and 37 for pMMEG* and on days 0 and 30 for pFRG*. For this calculation first order rate-of-loss model was used: rate of loss $\lambda=(-1/t)(\ln N_t/N_o)$. $N_o$ is the percentage of the green cells at the beginning of the experiment of non-selective conditions and Nt is the percentage of the green cells after t generations.

Expression of luciferase analysis. The expression analysis was done in CHO4.15 E2 cell line with plasmids carrying different regulatory elements and recombinant EGFP-luciferase gene. The cells were electroporated with the equimolar amounts of the EGFP-luciferase vectors. For negative control the cells were transfected with carrier DNA only. In different time-point, the cells were washed with PBS and lyzed with appropriate amount of 1*CCLR ragent (Promega). Luciferase activities in the samples were measured using Luciferase Assay System kit (Promega) and plate reading luminometer (Tecan). Different dilutions of the samlples in 1*CCLR buffer were used for verifying that all measurements are done at linear range. For normalisation of the activities of to the total protein in the samples, these were diluted 4 times with water. Thereafter, BCA assay kit (Pierce) was uded for measuments.

REFERENCES

1. Abroi, A., I. Ilves, S. Kivi, and M. Ustav. 2004. Analysis of chromatin attachment and partitioning functions of bovine papillomavirus type 1 E2 protein. Journal of Virology 78:2100-13.
2. Ilves, I., S. Kivi, and M. Ustav. 1999. Long-term episomal maintenance of bovine papillomavirus type 1 plasmids is determined by attachment to host chromosomes, which Is mediated by the viral E2 protein and its binding sites. Journal of Virology 73:4404-12.
3. Kurg, R., J. Parik, E. Juronen, T. Sedman, A. Abroi, I. Liiv, U. Langel, and M. Ustav. 1999. Effect of bovine papillomavirus E2 protein-specific monoclonal antibodies on papillomavirus DNA replication. Journal of Virology 73:4670-7.
4. Mannik, A., M. Piirsoo, K. Nordstrom, E. Ustav, B. Vennstrom, and M. Ustav. 2003. Effective generation of transgenic mice by Bovine papillomavirus type 1 based self-replicating plasmid that is maintained as extrachromosomal genetic element in three generations of animals. Plasmid 49:193-204.
5. Morgenstern, J. P., and H. Land. 1990. Advanced mammalian gene transfer: high titre retroviral vectors with multiple drug selection markers and a complementary helper-free packaging cell line. Nucleic Acids Research 18:3587-96.
6. Nilsson, M., M. Forsberg, Z. Y. You, G. Westin, and G. Magnusson. 1991. Enhancer effect of bovine papillomavirus E2 protein in replication of polyomavirus DNA. Nucleic Acids Research 19:7061-5.
7. Piirsoo, M., E. Ustav, T. Mandel, A. Stenlund, and M. Ustav. 1996. Cis and trans requirements for stable episomal maintenance of the BPV-1 replicator. EMBO Journal 15:1-11.

8. Tyndall, C., G. La Mantia, C. M. Thacker, J. Favaloro, and R. Kamen. 1981. A region of the polyoma virus genome between the replication origin and late protein coding sequences is required in cis for both early gene expression and viral DNA replication. Nucleic Acids Research 9:6231-50.
9. Ustav E, Ustav M, Szymanski P, Stenlund A. 1993 The bovine papillomavirus origin of replication requires a binding site for the E2 transcriptional activator. Proc. Natl. Acad. Sci. USA 90 (3): 898-902
10. Ustav, M., and A. Stenlund. 1991. Transient replication of BPV-1 requires two viral polypeptides encoded by the E1 and E2 open reading frames. EMBO Journal 10:449-57.
11. Wade-Martins, R., J. Frampton, and M. R. James. 1999. Long-term stability of large insert genomic DNA episomal shuttle vectors in human cells. Nucleic
12. Guo, Z. S., and M. L. DePamphilis. 1992. Specific transcription factors stimulate simian virus 40 and polyomavirus origins of DNA replication. Mol Cell Biol 12:2514-24. Acids Research 27:1674-82.
13. Hung, S. C., M. S. Kang, and E. Kieff. 2001. Maintenance of Epstein-Barr virus (EBV) oriP-based episomes requires EBV-encoded nuclear antigen-1 chromosome-binding domains, which can be replaced by high-mobility group-I or histone H1. Proceedings of the National Academy of Sciences of the United States of America 98:1865-70.

What is claimed is:

1. An expression system to provide extended episomal replication of hybrid plasmids in eukaryotic cell lines, said system comprising:
   a) a vector having a mouse polyoma virus core origin obtained from a complete polyoma virus origin by removing enhancer element; a papillomavirus minichromosomal maintenance element (MME), said MME being a Bovine papillomavirus (BPV) MME and containing at least 5 E2-binding sites, said E2-binding sites being SEQ ID NO:9; an optional selection marker; and a gene of interest operably linked within an expression cassette expressing the gene in a eukaryotic cell; and
   b) a compatible cell line, wherein the vector is expressed, said cell line constitutively expressing BPV-E2 protein and mouse polyomavirus (PyV) LT protein either in presence or in absence of selective pressure.

2. The system according to claim 1, wherein the expression of BPV E2 and PyV LT in the cell line is provided by a vector or vectors comprising coding sequences of BPV E2 and PyV LT proteins.

3. The system according to claim 1, wherein the core origin is SEQ ID NO: 2.

4. The system according to claim 1, wherein the cell line is of mouse, hamster or human origin.

5. The system according to claim 4, wherein the cell line is selected from the group consisting of Chinese hamster ovary cells (CHO), mouse COP5 cell line and human cell line 293.

6. The expression system of claim 1, wherein the MME contains 10 E2-binding sites of SEQ ID NO:9.

7. An expression system to provide extended episomal replication of hybrid plasmids in eukaryotic cell lines, said system comprising:
   a) a first vector having a mouse polyoma virus core origin obtained from a complete polyoma virus origin by removing enhancer element; a papillomavirus MME, said MME being a BPV MME and containing at least 5 E2-binding sites being SEQ ID NO:9; an optional selection marker; and first gene of interest operably linked within eukaryotic expression cassette expressing the gene in a eukaryotic cell;
   b) a second vector having a mouse polyoma virus core origin obtained from a complete polyoma virus origin by removing enhancer element, an FR element of EBV, an optional selection marker, and a second gene of interest operably linked within an expression cassette expressing the gene in a eukaryotic cell; and
   c) a compatible cell line wherein the vectors are expressed, said cell line constitutively expressing BPV E2 protein, EBV EBNA1 protein and PyV LT protein either in presence or in absence of selective pressure.

8. The system according to claim 7, wherein the expression of BPV E2, EBV EBNA1 and PyV LT in the cell line is provided by a vector or vectors comprising coding sequences of BPV E2, EBV EBNA1 and PyV LT proteins.

9. The system according to claim 7, wherein the FR element comprises at least 16 EBNA 1 binding sites.

10. The system according to claim 9, wherein the EBNA1 binding sites are selected from the group consisting of SEQ ID NO:s 10,12 and 13.

11. The system according to claim 7, wherein the core origin is SEQ ID NO: 2.

12. The system according to claim 7, wherein the cell line is of mouse, hamster or human origin.

13. The system according to claim 12, wherein the cell line is selected from the group consisting of CHO, COP5 and human cell line 293.

14. The system according to claim 7, wherein the system additionally includes:
   a third vector, said third vector comprising a minimum core origin of a papillomavirus, a papillomavirus MME and, a third gene of interest operably linked within an expression cassette expressing the gene in a eukaryotic cell; and
   the cell line constitutively expresses BPV E2 protein, BPV E1 protein, EBV EBNA1 protein and Py LT protein.

15. The system according to claim 14, wherein the expression of BPV E2, BPV E1, EBV EBNA1 and PyV LT in the cell line is provided by a vector or vectors comprising coding sequences of BPV E1, BPV E2, EBV EBNA2 and PyV LT proteins.

16. The system according to claim 15, wherein the system additionally includes a fourth vector, said fourth vector comprising:
   a minimum core origin of a papillomavirus,
   an EBV FR-element; and
   a fourth gene of interest operably linked within an expression cassette regions expressing the gene in a eukaryotic cell.

* * * * *

UNITED STATES PATENT AND TRADEMARK OFFICE
CERTIFICATE OF CORRECTION

PATENT NO. : 7,790,446 B2  Page 1 of 1
APPLICATION NO. : 11/351809
DATED : August 10, 2010
INVENTOR(S) : Wu et al.

It is certified that error appears in the above-identified patent and that said Letters Patent is hereby corrected as shown below:

In item (73) change Assignee to: Icosagen Cell Factory Oü.

Signed and Sealed this

Fourteenth Day of December, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,790,446 B2 | |
| APPLICATION NO. | : 11/351809 | |
| DATED | : August 10, 2010 | |
| INVENTOR(S) | : Toomas Silla et al. | |

It is certified that error appears in the above-identified patent and that said Letters Patent is hereby corrected as shown below:

Title Page, in item (73) change Assignee to: Icosagen Cell Factory Oü.

This certificate supersedes the Certificate of Correction issued December 14, 2010.

Signed and Sealed this
Twenty-second Day of March, 2011

David J. Kappos
*Director of the United States Patent and Trademark Office*